(12) United States Patent
Veitch et al.

(10) Patent No.: US 11,094,398 B2
(45) Date of Patent: Aug. 17, 2021

(54) METHODS FOR CALCULATING CORRECTED AMPLICON COVERAGES

(71) Applicant: LIFE TECHNOLOGIES CORPORATION, Carlsbad, CA (US)

(72) Inventors: James Veitch, Berkeley, CA (US); Yiping Zhan, South San Francisco, CA (US)

(73) Assignee: Life Technologies Corporation, Carlsbad, CA (US)

(*) Notice: Subject to any disclaimer, the term of this patent is extended or adjusted under 35 U.S.C. 154(b) by 1335 days.

(21) Appl. No.: 14/879,533

(22) Filed: Oct. 9, 2015

(65) Prior Publication Data

US 2016/0103957 A1 Apr. 14, 2016

Related U.S. Application Data

(60) Provisional application No. 62/062,312, filed on Oct. 10, 2014.

(51) Int. Cl.
| | | |
|---|---|---|
| G16B 40/00 | (2019.01) | |
| G16B 30/00 | (2019.01) | |
| G16B 20/00 | (2019.01) | |
| C12Q 1/6869 | (2018.01) | |

(52) U.S. Cl.
CPC ........... *G16B 40/00* (2019.02); *C12Q 1/6869* (2013.01); *G16B 20/00* (2019.02); *G16B 30/00* (2019.02)

(58) Field of Classification Search
None
See application file for complete search history.

(56) References Cited

U.S. PATENT DOCUMENTS

| | | | |
|---|---|---|---|
| 5,427,910 | A | 6/1995 | Kamentsky et al. |
| 6,465,182 | B1 | 10/2002 | Gray et al. |
| 7,636,636 | B2 | 12/2009 | Piper |
| 7,704,687 | B2 | 4/2010 | Wang et al. |
| 7,776,536 | B2 | 8/2010 | Pinkel et al. |
| 7,888,024 | B2 | 2/2011 | Hosono et al. |
| 7,937,225 | B2 | 5/2011 | Mishra et al. |
| 8,190,373 | B2 | 5/2012 | Huang et al. |
| 8,551,707 | B2 | 10/2013 | Oeth et al. |
| 8,554,488 | B2 | 10/2013 | Wigler et al. |
| 8,655,599 | B2 | 2/2014 | Chinitz et al. |
| 8,712,697 | B2 | 4/2014 | Struble |
| 8,722,327 | B2 | 5/2014 | Cao et al. |
| 8,725,422 | B2 | 5/2014 | Halpern et al. |
| 8,852,865 | B2 | 10/2014 | Endress et al. |
| 2003/0082618 | A1 | 5/2003 | Li et al. |
| 2006/0057618 | A1 | 3/2006 | Piper et al. |
| 2007/0174008 | A1 | 7/2007 | Yakhini et al. |
| 2008/0021660 | A1 | 1/2008 | Shukla et al. |
| 2008/0090237 | A1 | 4/2008 | Yakhini et al. |
| 2008/0120038 | A1 | 5/2008 | Ghosh et al. |
| 2008/0125979 | A1 | 5/2008 | Yakhini et al. |
| 2009/0026082 | A1 | 1/2009 | Rothberg et al. |
| 2009/0035764 | A1 | 2/2009 | Sampas |
| 2009/0127589 | A1 | 5/2009 | Rothberg et al. |
| 2009/0136918 | A1 | 5/2009 | Newkirk |
| 2009/0270270 | A1 | 10/2009 | Rouleau et al. |
| 2009/0325145 | A1 | 12/2009 | Sablon et al. |
| 2010/0137143 | A1 | 6/2010 | Rothberg et al. |
| 2010/0197507 | A1 | 8/2010 | Rothberg et al. |
| 2010/0228496 | A1 | 9/2010 | Leong et al. |
| 2010/0300559 | A1 | 12/2010 | Schultz et al. |
| 2010/0300895 | A1 | 12/2010 | Nobile et al. |
| 2010/0301398 | A1 | 12/2010 | Rothberg et al. |
| 2011/0091900 | A1 | 4/2011 | Williams et al. |
| 2011/0111419 | A1 | 5/2011 | Stefansson et al. |
| 2011/0177517 | A1 | 7/2011 | Rava et al. |
| 2011/0207612 | A1 | 8/2011 | Park et al. |
| 2011/0257896 | A1 | 10/2011 | Dowds et al. |
| 2012/0046877 | A1 | 2/2012 | Hyland et al. |
| 2012/0059594 | A1 | 3/2012 | Hatchwell et al. |
| 2012/0095697 | A1 | 4/2012 | Halpern et al. |
| 2012/0184449 | A1 | 7/2012 | Hixson et al. |
| 2012/0215459 | A1 | 8/2012 | Stef et al. |
| 2012/0220478 | A1 | 8/2012 | Shaffer |

(Continued)

FOREIGN PATENT DOCUMENTS

| | | |
|---|---|---|
| WO | 2006/084131 | 8/2006 |
| WO | 2012/044847 | 4/2012 |

(Continued)

OTHER PUBLICATIONS

Affymetrix, "CNAT 4.0: Copy Number and Loss of Heterozygosity Estimation Algorithms for the GeneChip® Human Mapping 10/50/100/250/500K Array Set," Revision Version 1.2, Affymetrix, Inc., pp. 1-26 (dated Mar. 13, 2007).

Affymetrix, "High-Resolution Chromosome Copy Number Analysis Using GeneChip® Mapping Arrays," Technical Note, GeneChip® Chromosome Copy Number Analysis Tool, Affymetrix, Inc., pp. 1-7 (2005).

Affymetrix, "Affymetrix GeneChip® Chromosome Copy Number Analysis Tool (CNAT)—Version 4.0," User Guide, Affymetrix, Inc., 102 pages (dated Mar. 2006).

Barnes et al., "A robust statistical method for case-control association testing with copy number variation," *Nat. Genet.*, 40(10):1245-1252 (Oct. 2008).

(Continued)

*Primary Examiner* — Joseph Woitach

(57) ABSTRACT

Methods, systems, and computer-readable media are disclosed for calculating corrected amplicon coverages. One method includes: mapping a plurality of reads of a plurality of amplicons based on amplified target regions of a sample suspected of having one or more genetic abnormalities to a reference sequence that includes one or more nucleic acid sequences corresponding to the amplified target regions; calculating amplicon coverages and total reads, wherein amplicon coverages is a number of reads mapped to an amplicon, and total reads is a number of mapped reads; and calculating corrected amplicon coverages based on the calculated amplicon coverages and calculated total reads by applying a batch effect correction.

6 Claims, 38 Drawing Sheets

(56) References Cited

U.S. PATENT DOCUMENTS

| | | | |
|---|---|---|---|
| 2012/0225791 | A1 | 9/2012 | Zamboni et al. |
| 2012/0245050 | A1 | 9/2012 | Hiroi et al. |
| 2012/0295819 | A1 | 11/2012 | Leamon et al. |
| 2013/0079423 | A1 | 3/2013 | Abkevich et al. |
| 2013/0122499 | A1 | 5/2013 | Morris et al. |
| 2013/0178389 | A1 | 7/2013 | Lapidus et al. |
| 2013/0179086 | A1 | 7/2013 | Leong et al. |
| 2013/0197812 | A1 | 8/2013 | Palo |
| 2013/0261983 | A1 | 10/2013 | Dzakula et al. |
| 2014/0024538 | A1 | 1/2014 | Zahn et al. |
| 2014/0051154 | A1 | 2/2014 | Hyland et al. |
| 2014/0256571 | A1 | 9/2014 | Konvicka |
| 2014/0274740 | A1 | 9/2014 | Srinivasan et al. |
| 2014/0274745 | A1 | 9/2014 | Chen et al. |
| 2015/0012252 | A1 | 1/2015 | Yin et al. |
| 2015/0038336 | A1 | 2/2015 | Barany et al. |
| 2015/0094212 | A1 | 4/2015 | Gottimukkala et al. |
| 2015/0310165 | A1 | 10/2015 | Mann |

FOREIGN PATENT DOCUMENTS

| | | |
|---|---|---|
| WO | 2014/138153 | 9/2014 |
| WO | 2014/165596 | 10/2014 |
| WO | 2016/061111 | 4/2016 |

OTHER PUBLICATIONS

Bierut et al., "Novel Genes Identified in a High Density Genome Wide Association Study for Nicotine Dependence," *Hum. Mol. Genet.*, 16(1):24-35 (Jan. 1, 2007).

Chen et al., "A Pipeline for Copy Number Variation Detection based on Principal Component Analysis," *Conf. Proc. IEEE Eng. Med. Biol. Soc.*, 2011:6975-6978 (2011).

Chu et al., "Copy Number variation genotyping using family information," *BMC Bioinformatics*, 14:157, pp. 1-11 (2013).

Fromer et al., "Discovery and Statistical Genotyping of Copy-Number Variation from Whole-Exome Sequencing Depth," *Am. J. Hum. Genet.*, 91:597-607 (Oct. 5, 2012).

Hinds et al., "Matching Strategies for Genetic Association Studies in Structured Populations," *Am. J. Hum. Genet.*, 74:317-325 (2004).

Ivakhno et al., "CNAseg-a novel framework for identification of copy number changes in cancer from second-generation sequencing data," *Bioinformatics*, 26(24):3051-3058 (2010).

Jacobs et al., "Genome-Wide, High-Resolution Detection of Copy Number, Loss of Heterozygosity, and Genotypes from Formalin-Fixed Paraffin-Embedded Tumor Tissue Using Microarrays," *Cancer Res.*, 67(6):2544-2551 (Mar. 15, 2007).

Lee et al., "Reducing system noise in copy number data using principal components of self-self hybridizations," *PNAS*, 109(3):E103-E110 (Jan. 17, 2012).

Magi et al., "Detecting common copy number variants in high-throughput sequencing data by using JointSLM algorithm," *Nucleic Acids Research*, 39(10):e65, pp. 1-9 (Feb. 14, 2011).

Marioni et al., "BioHMM: a heterogeneous hidden Markov model for segmenting array CGH data," *Bioinformatics*, 22(9):1144-1146 (2006).

McCarroll et al., "Integrated detection and population-genetic analysis of SNPs and copy number variation," *Nat. Genet.*, 40(10):1166-1174 (Oct. 2008).

Medvedev et al., "Computational Methods for Discovering Structural Variation with Next-Generation Sequencing," *Nat. Methods Suppl.*, 6:S13-S20 (2009).

Nannya et al., "A Robust Algorithm for Copy Number Detection Using High-Density Oligonucleotide Single Nucleotide Polymorphism Genotyping Arrays", *Cancer Res.*, 65(14):6071-6079 (Jul. 15, 2005).

PCT/US2015/054910, International Search Report and Written Opinion dated Jan. 2016, 11 pages.

Peters et al., "Accurate whole genome sequencing and haplotyping from 10-20 human cells," *Nature*, 487(7406):190-195 (2012).

Reese et al., "A new statistic for identifying batch effects in high-throughput genomic data that uses guided principle component analysis," *Bioinformatics*, 29(22):2877-2883 (Aug. 19, 2013).

Risso et al., "GC-Content Normalization for RNA-Seq Data," *BMC Bioinformatics*, 12:480, pp. 1-17 (2011).

Wang et al., "Copy number variation detection using next generation sequencing read counts," *BMC Bioinformatics*, 15:109, pp. 1-14 (2014).

Wineinger et al., "Statistical issues in the analysis of DNA Copy Number Variations," *Int. J. Comput. Biol. Drug Des.*, 1(4):368-395 (2008).

Xie et al., "CNV-seq, a new method to detect copy number variation using high-throughput sequencing," *BMC Bioinformatics*, 10:80, pp. 1-9 (Mar. 6, 2009).

Yoon et al., "Sensitive and accurate detection of copy number variants using read depth of coverage," *Genome Res.*, 19:1586-1592 (2009).

EP15848233.1, Extended European Search Report dated May 7, 2018, 7 pp.

Leek, J. et al., "Tackling the widespread and critical impact of batch effects in high-throughput data", *Nature Reviews Genetics*, vol. 11, No. 10, XP055470890, DOI:10.1038/nrg2825, Sep. 14, 2010, 733-739.

Reese, S. et al., "Detecting and Correcting Batch Effects in High-Throughput Genomic Experiments", *Virginia Commonwealth University, Theses and Dissertations*, XP055471251, Jan. 1, 2013, 136 pp.

Ion Reporter, CNV Algorithm; White Paper. Thermo Fisher Scientific. 2014.

Ion Reporter, CNV Workflow; White Paper. Thermo Fisher Scientific. 2014.

CNV-Detection-by-Ion.pdf https://tools.thermofisher.com/content/sfs/brochures/CNV-Detection-by-Ion.pdf. Thermo Fisher Scientific. 2014.

Wang et al. PennCNV: An integrated hidden Markov model designed for high-resolution copy number variation detection in whole-genome SNP genotyping data. Genome Research 17:1665-1674 Oct. 5, 2007. ISSN 1088-9051/07; http://www.genome.org/cgi/doi/10.1101/gr.6861907.

MAPD = 0.47

MAPD = 0.74

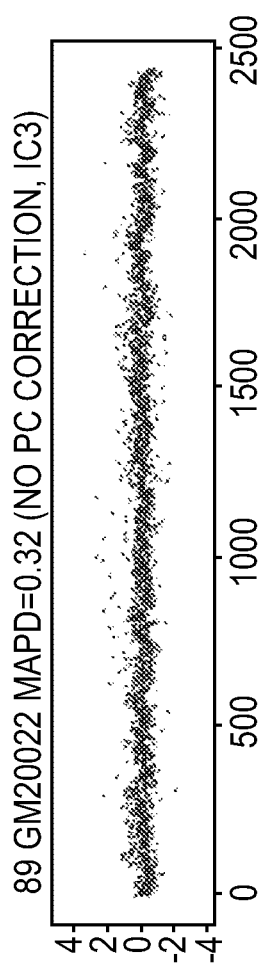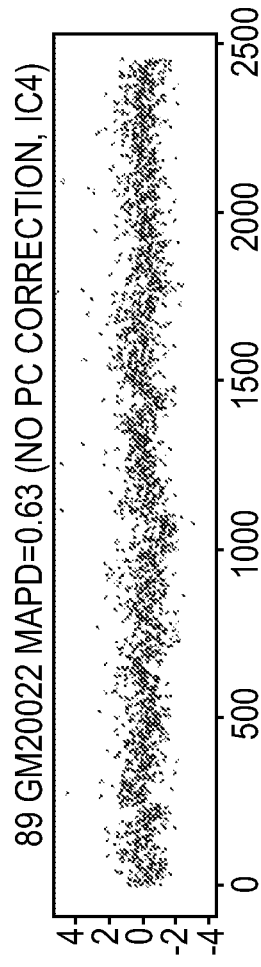

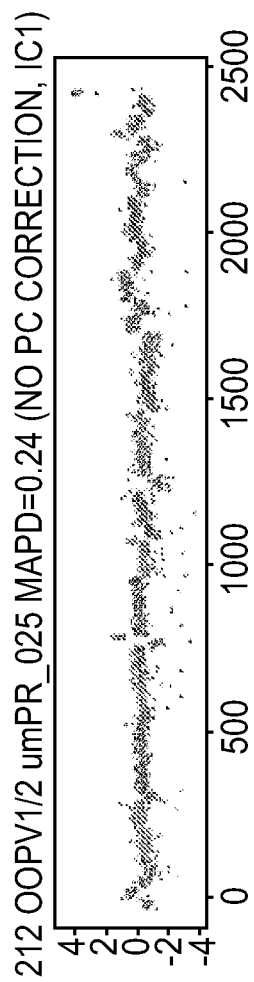
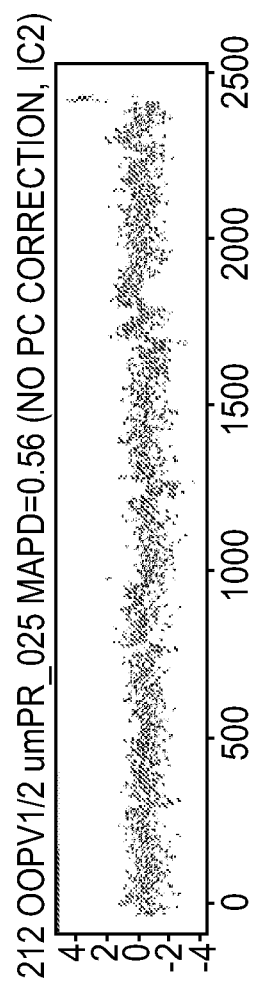
FIG. 15A
FIG. 15B

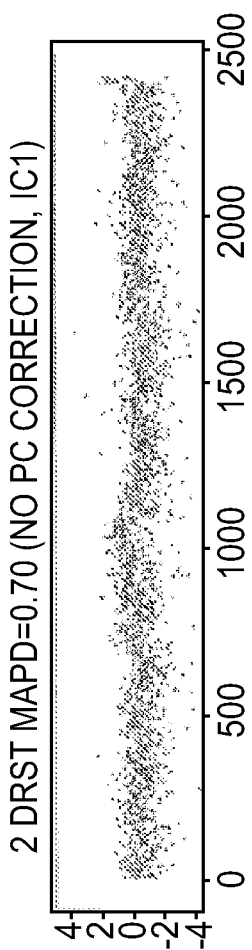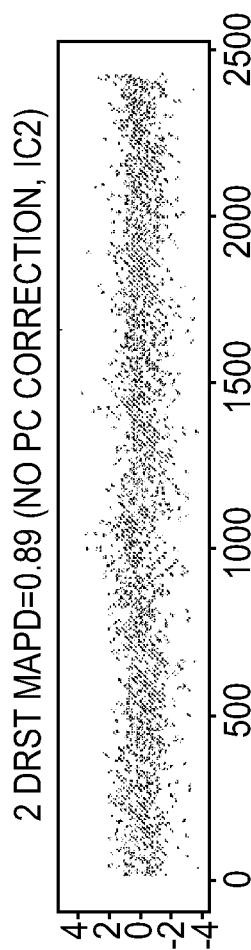

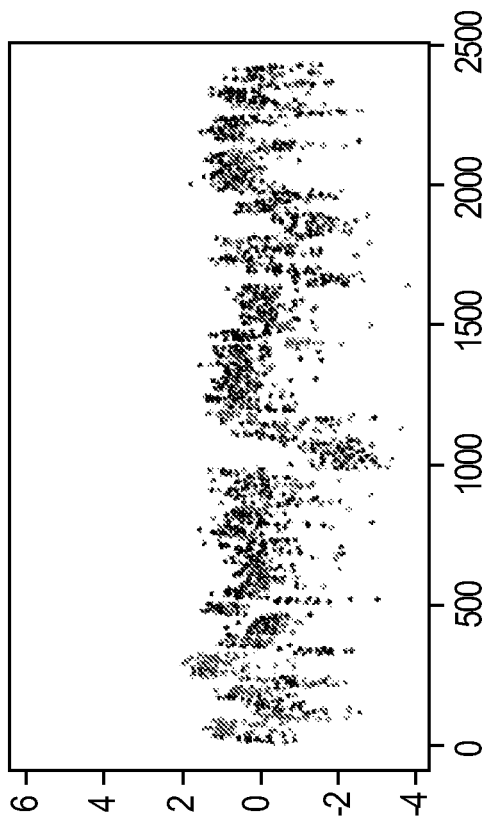
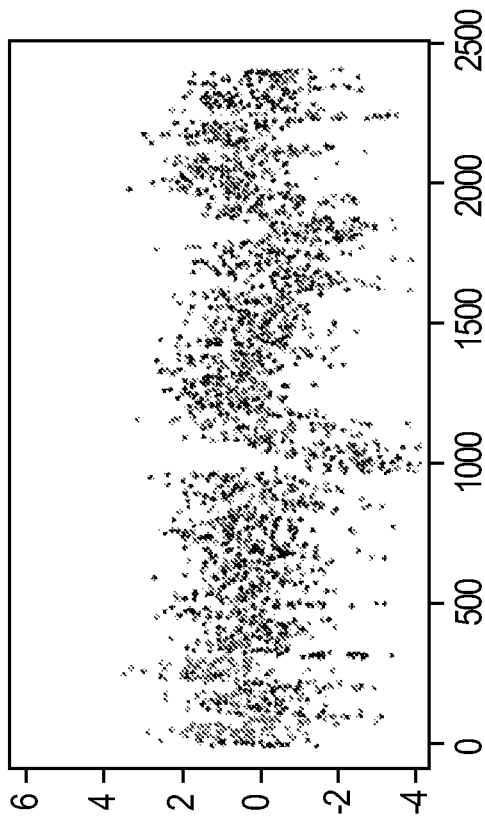
FIG. 19B
FIG. 19A

METHODS FOR CALCULATING CORRECTED AMPLICON COVERAGES

CROSS-REFERENCE TO RELATED APPLICATIONS

This application claims priority under 35 U.S.C. § 119(e) to U.S. Provisional Application No. 62/062,312, filed Oct. 10, 2014, entitled "Systems and Methods for Identifying Copy Number Variation," the contents of the foregoing application is incorporated herein by reference in its entirety.

FIELD OF THE DISCLOSURE

The present disclosure generally relates to the field of nucleic acid sequencing including systems, methods, and computer-readable media for calculating corrected amplicon coverages, and more particularly to identifying copy number variation based on corrected amplicon coverages.

BACKGROUND

Upon completion of the Human Genome Project, one focus of the sequencing industry has shifted to finding higher throughput and/or lowering the cost of nucleic acid sequencing technologies, sometimes referred to as "next generation" sequencing ("NGS") technologies. In increasing the throughput of sequencing and/or decreasing the cost of sequencing, a goal is to make the technology more accessible. This goal, among others, may be reached through the use of sequencing platforms and/or methods that provide sample preparation for samples of significant complexity, sequencing larger numbers of samples in parallel (for example, through use of barcodes and multiplex analysis), and/or processing high volumes of information efficiently and completing the analysis in a timely manner. Various methods, such as, for example, sequencing by synthesis, sequencing by hybridization, and sequencing by ligation are evolving to meet these challenges.

Ultra-high throughput nucleic acid sequencing systems incorporating NGS technologies may typically produce a large number of short sequence reads. Sequence processing methods should desirably assemble and/or map a large number of reads quickly and efficiently, such as to minimize use of computational resources. For example, data arising from sequencing of a mammalian genome may result in tens or hundreds of millions of reads that typically need to be assembled before they can be further analyzed to determine their biological, diagnostic, and/or therapeutic relevance.

Exemplary applications of NGS technologies include, but are not limited to: genomic variant detection (such as insertions/deletions, copy number variations, single nucleotide polymorphisms, etc.), genomic resequencing, gene expression analysis, and genomic profiling.

Copy number variations ("CNVs") may be indicative of large scale chromosomal rearrangements (such as large insertions or deletions), which can be commonly found in cancer tissue. In some cases, entire chromosomes can be lost and/or duplicated (aneuploidy), which is a common cause of genetic disorders, such as Down's syndrome (trisomy 21), cat eye syndrome (trisomy 22), Williams syndrome (monosomy 7), and various other genetic disorders. Identifying copy number variations may help understand and diagnose cancer and aneuploidy genetic disorders.

From the foregoing, it may be appreciated that a need exists for systems and methods that may identify and determine copy number variations.

SUMMARY OF THE DISCLOSURE

Embodiments disclose apparatuses, methods, systems, and computer-readable media for calculating corrected amplicon coverages. The following methods, systems, computer-readable media, and devices are exemplified in a number of implementations, some of which are summarized below and throughout the specification.

In one aspect of the present disclosure, a computer-implemented method for calculating corrected amplicon coverages is disclosed. One method comprises: mapping a plurality of reads of a plurality of amplicons based on amplified target regions of a sample suspected of having one or more genetic abnormalities to a reference sequence, the reference sequence including one or more nucleic acid sequences corresponding to the amplified target regions; calculating amplicon coverages and total reads, wherein amplicon coverages is a number of reads mapped to an amplicon, and total reads is a number of mapped reads; and calculating corrected amplicon coverages based on the calculated amplicon coverages and calculated total reads by applying a batch effect correction.

In one aspect of the present disclosure, a system for calculating corrected amplicon coverages is disclosed. One system includes: a data storage device that stores instructions system for calculating corrected amplicon coverages; and a processor configured to execute the instructions to perform a method including: mapping a plurality of reads of a plurality of amplicons based on amplified target regions of a sample suspected of having one or more genetic abnormalities to a reference sequence, the reference sequence including one or more nucleic acid sequences corresponding to the amplified target regions; calculating amplicon coverages and total reads, wherein amplicon coverages is a number of reads mapped to an amplicon, and total reads is a number of mapped reads; and calculating corrected amplicon coverages based on the calculated amplicon coverages and calculated total reads by applying a batch effect correction.

In one aspect of the present disclosure, a non-transitory computer-readable medium storing instructions that, when executed by a computer, cause the computer to perform a method for calculating corrected amplicon coverages is disclosed. The method of the non-transitory computer-readable medium includes: mapping a plurality of reads of a plurality of amplicons based on amplified target regions of a sample suspected of having one or more genetic abnormalities to a reference sequence, the reference sequence including one or more nucleic acid sequences corresponding to the amplified target regions; calculating amplicon coverages and total reads, wherein amplicon coverages is a number of reads mapped to an amplicon, and total reads is a number of mapped reads; and calculating corrected amplicon coverages based on the calculated amplicon coverages and calculated total reads by applying a batch effect correction.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims.

It is to be understood that both the foregoing general description and the following detailed description are exemplary and explanatory only and are not restrictive of the scope of disclosed embodiments, as set forth by the claims.

BRIEF DESCRIPTION OF THE DRAWINGS

The accompanying drawings, which are incorporated into and form a part of the specification, illustrate one or more exemplary embodiments and serve to explain the principles of various exemplary embodiments. The drawings are exemplary and explanatory only and are not to be construed as limiting or restrictive in any way.

FIGS. 13A-13E depict graphs illustrating comparisons of example samples with and without batch effects correction, in accordance with various embodiments of the present disclosure;

FIGS. 15A-15E depict graphs illustrating comparisons of example samples with and without batch effects correction, in accordance with various embodiments of the present disclosure;

FIGS. 16A-16E depict graphs illustrating comparisons of example samples with and without batch effects correction, in accordance with various embodiments of the present disclosure;

FIGS. 19A and 19B depict graphs illustrating comparisons of example samples with and without pre-preprocessing, in accordance with various embodiments of the present disclosure;

Figure 1:
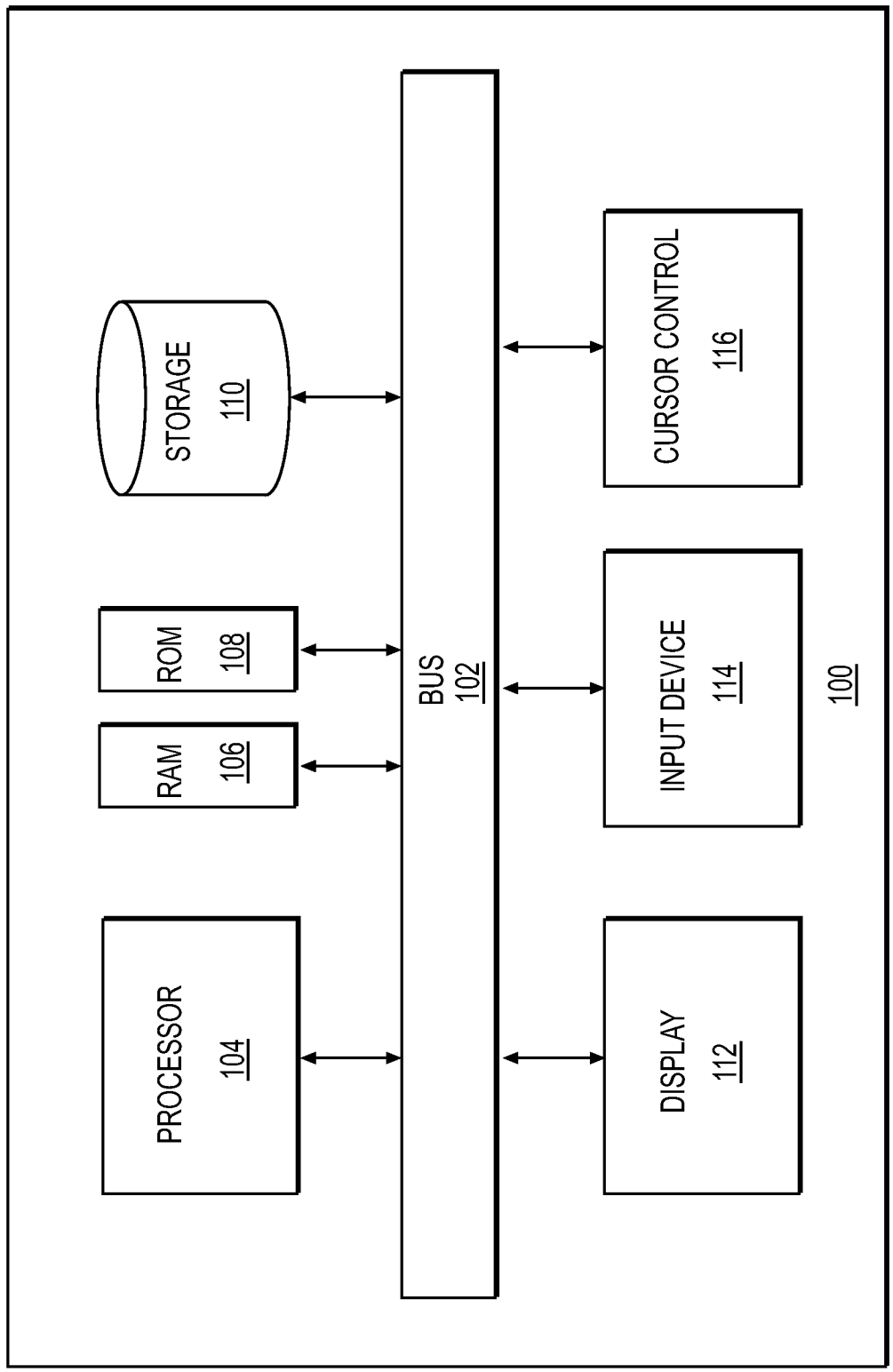
FIG. 1 depicts a block diagram that illustrates an exemplary computer system, in accordance with various embodiments of the present disclosure.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DETAILED DESCRIPTION OF EMBODIMENTS

The following description and the various embodiments described herein are exemplary and explanatory only and are not to be construed as limiting or restrictive in any way. Other embodiments, features, objects, and advantages of the present teachings will be apparent from the description and accompanying drawings, and from the claims. In this detailed description of embodiments section, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

Embodiments of systems and methods for detecting copy number variations are described herein.

The section headings used herein are for organizational purposes only and are not to be construed as limiting the described subject matter in any way.

All literature and similar materials cited in this application, including but not limited to, patents, patent applications, articles, books, treatises, and Internet web pages are expressly incorporated by reference in their entirety for any purpose. Unless described otherwise, all technical and scientific terms used herein have a meaning as is commonly understood by one of ordinary skill in the art to which the various embodiments described herein belongs.

It will be appreciated that there is an implied "about" prior to the temperatures, concentrations, times, number of bases, coverage, etc. discussed in the present disclosure, such that slight and insubstantial deviations are within the scope of the present disclosure. In the present disclosure, the use of the singular includes the plural unless specifically stated otherwise. Also, the use of "comprise", "comprises", "comprising", "contain", "contains", "containing", "include", "includes", and "including" are not intended to be limiting. It is to be understood that both the foregoing general description and the following detailed description are exemplary and explanatory only and are not restrictive of the present disclosure.

As used herein, "a" or "an" also may refer to "at least one" or "one or more." Also, the use of "or" is inclusive, such that the phrase "A or B" is true when "A" is true, "B" is true, or both "A" and "B" are true.

Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well-known and commonly used in the art. Standard techniques are used, for example, for nucleic acid purification and preparation, chemical analysis, recombinant nucleic acid, and oligonucleotide synthesis. Enzymatic reactions and purification techniques are performed according to manufacturer's specifications or as commonly accomplished in the art or as described herein. The techniques and procedures described herein may generally be performed according to conventional methods well known in the art and as described in various general and more specific references that are cited and discussed throughout the present disclosure. See, e.g., Sambrook et al., Molecular Cloning: A Laboratory Manual (Third ed., Cold Spring Harbor Laboratory Press, Cold Spring Harbor, N.Y. 2000). The laboratory procedures and techniques described herein, and the nomenclatures utilized in connection therewith, are those well-known and commonly used in the art.

In various embodiments, unknown yet systematic differences in amplification efficiency (also referred to as "batch effects") may result in variations in amplification efficiencies of the same sequence of DNA between different batches of samples. These variations may be the result of differences in sample preparation conditions, such as differences in conditions like changes in concentration and/or pH in various solutions used during sample preparation and/or differences in the temperature. These variations may also be caused by differences in sample handling conditions like allowing the sample to sit overnight versus running the sample immediately.

Batch effects may be detected and may be removed using principal components analysis ("PCA"). PCA is a technique in copy number ("ON") determination using microarrays that may also be applied to targeted NGS assays. Principal components analysis may depend on three assumptions. First, for PCA, there may be a need to have multiple samples with a known copy number (e.g., a set of non-tumor normal samples) that exhibit these batch effects to a greater or lesser degree. Second, most of the genomic positions in each sample is of the known copy number (e.g., 2 in autosomes, and 1 or 2 in sex chromosomes). Finally, adjacent positions in the sample are likely to share the same copy number. The set of normal samples may be used to discover the batch effects after which each sample may be corrected and/or adjusted by estimating a size of the batch effect and correcting and/or adjusting the size. In another embodiment, a set of non-normal samples may be used to discover the batch effects.

For any given genomic location, determination of a copy number may depend on the measured value being determined by the underlying copy number of the DNA at that location. If an assay preserves a relative copy number of DNA in an input sample at a given genomic location and the readout is quantitative, then the copy number may be determined in the input sample.

For example, for a single nucleotide polymorphism ("SNP") microarray, there may be fragmentation of input DNA, followed by a linear amplification and a quantitative fluorescence hybridization readout where each oligonucleotide probe has a specific binding to DNA in a particular genomic location. For multiplex amplification assays, there may be an amplicon-specific PCR amplification of input DNA and counting of the resultant product using a next-generation sequencer, such as an Ion Torrent Personal Genome Machine ("PGM"). Amplification efficiency for each genomic location may be empirically accounted by running a set of samples with a known copy number (i.e., normals) and per-sample adjustments due to known covariates, such as guanine-cytosine content ("GC-content"), and/or fragment length may be estimated and accounted for.

However, there may be other batch effects that are of unknown cause. Using principal component analysis on a set of samples may be used to discover such batch effects. Then the batch effects may be removed on a per sample basis by estimating the per-sample magnitude and subtracting the per-sample magnitude out. This technique may work for samples where the majority of genomic positions are expected to be of the known copy number.

In various embodiments, the variations in amplification efficiency may increase batch-to-batch variability of a determined copy number, leading to a less reliable determination. Applying a correction for the batch effects may reduce batch-to-batch variability and may improve the reliability of the copy number determination. In various embodiments, some batch effects may be avoided by placing stringent controls on sample preparation solutions and conditions, which may require validation of each lot of sample preparation reagents. Computationally correcting for the batch effects may reduce the requirement for stringent controls and validation of reagent lots, thereby reducing time and costs associated with accurate copy number determination. Additionally, computational techniques may ensure batch-to-batch consistency of copy number determination even when factors other than lot-to-lot reagent variability are not the cause.

A "system" sets forth a set of components, comprising a whole where each component interacts with or is related to at least one other component within the whole.

A "biomolecule" may refer to any molecule that is produced by a biological organism, including large polymeric molecules such as proteins, polysaccharides, lipids, and nucleic acids (DNA and RNA) as well as small molecules such as primary metabolites, secondary metabolites, and other natural products.

The phrase "next generation sequencing" or NGS refers to sequencing technologies having increased throughput as compared to traditional Sanger- and capillary electrophoresis-based approaches, for example with the ability to generate hundreds of thousands of relatively small sequence reads at a time. Some examples of next generation sequencing techniques include, but are not limited to, sequencing by synthesis, sequencing by ligation, and sequencing by hybridization. More specifically, the Personal Genome Machine ("PGM") of Life Technologies Corp. provides massively parallel sequencing with enhanced accuracy. The PGM System and associated workflows, protocols, chemistries, etc. are described in more detail in U.S. Patent Application Publication No. 2009/0127589 and No. 2009/0026082, the entirety of each of these applications being incorporated herein by reference.

The phrase "sequencing run" refers to any step or portion of a sequencing experiment performed to determine some information relating to at least one biomolecule (e.g., nucleic acid molecule).

The phase "base space" refers to a representation of the sequence of nucleotides. The phase "flow space" refers to a representation of the incorporation event or non-incorporation event for a particular nucleotide flow. For example, flow space can be a series of values representing a nucleotide incorporation events (such as a one, "1") or a non-incorporation event (such as a zero, "0") for that particular nucleotide flow. Nucleotide flows having a non-incorporation event can be referred to as empty flows, and nucleotide flows having a nucleotide incorporation event can be referred to as positive flows. It should be understood that zeros and ones are convenient representations of a non-incorporation event and a nucleotide incorporation event. However, any other symbol or designation could be used alternatively to represent and/or identify these events and non-events. In particular, when multiple nucleotides are incorporated at a given position, such as for a homopolymer stretch, the value can be proportional to the number of nucleotide incorporation events, and thus, the length of the homopolymer stretch.

Deoxyribonucleic acid ("DNA") is a chain of nucleotides consisting of 4 types of nucleotides; A (adenine), T (thymine), C (cytosine), and G (guanine), and that ribonucleic acid ("RNA") is comprised of 4 types of nucleotides; A, U (uracil), G, and C. Certain pairs of nucleotides specifically bind to one another in a complementary fashion (also referred to as, complementary base pairing). That is, adenine (A) pairs with thymine (T) (in the case of RNA, however, adenine (A) pairs with uracil (U)), and cytosine (C) pairs with guanine (G). When a first nucleic acid strand binds to a second nucleic acid strand made up of nucleotides that are complementary to those in the first strand, the two strands bind to form a double strand. As used herein, "nucleic acid sequencing data," "nucleic acid sequencing information," "nucleic acid sequence," "genomic sequence," "genetic sequence," "fragment sequence," or "nucleic acid sequencing read" denotes any information or data that is indicative of the order of the nucleotide bases (e.g., adenine, guanine, cytosine, and thymine/uracil) in a molecule (e.g., whole genome, whole transcriptome, exome, oligonucleotide, polynucleotide, fragment, etc.) of DNA or RNA. It should be understood that the present teachings contemplate sequence information obtained using all available varieties of techniques, platforms or technologies, including, but not limited to: capillary electrophoresis, microarrays, ligation-based systems, polymerase-based systems, hybridization-based systems, direct or indirect nucleotide identification systems, pyrosequencing, ion- or pH-based detection systems, electronic signature-based systems, etc.

A "polynucleotide," "nucleic acid," or "oligonucleotide" refers to a linear polymer of nucleosides (including deoxyribonucleosides, ribonucleosides, or analogs thereof) joined by internucleosidic linkages. Typically, a polynucleotide comprises at least three nucleosides. Usually oligonucleotides range in size from a few monomeric units, e.g., 3-4, to several hundreds of monomeric units. Whenever a polynucleotide, such as an oligonucleotide, is represented by a sequence of letters, such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, unless otherwise noted. The letters A, C, G, and T may be used to refer to the bases themselves, to nucleosides, or to nucleotides comprising the bases, as is standard in the art.

As used herein, a "somatic variation" or "somatic mutation" may refer to a variation in genetic sequence including a copy number change that results from a mutation that occurs in a non-germline cell. The variation may be passed on to daughter cells through mitotic division. This may result in a group of cells having a genetic difference from the rest of the cells of an organism. Additionally, as the variation does not occur in a germline cell, the mutation may not be inherited by progeny organisms.

As defined herein "multiplex amplification" refers to selective and non-random amplification of two or more target sequences within a sample using at least one target-specific primer. In some embodiments, multiplex amplification may be performed such that some or all of the target sequences are amplified within a single reaction vessel. The "plexy" or "plex" of a given multiplex amplification refers generally to the number of different target-specific sequences that are amplified during that single multiplex amplification. In some embodiments, the plexy can be about 12-plex, 24-plex, 48-plex, 96-plex, 192-plex, 384-plex, 768-plex, 1536-plex, 3072-plex, 6144-plex or higher.

Multiplex Amplification Methods:

In various embodiments, target nucleic acids generated by the amplification of multiple target-specific sequences from a population of nucleic acid molecules may be sequenced. In some embodiments, the amplification may include hybridizing one or more target-specific primer pairs to the target sequence, extending a first primer of the primer pair, denaturing the extended first primer product from the population of nucleic acid molecules, hybridizing to the extended first primer product the second primer of the primer pair, extending the second primer to form a double stranded product, and digesting the target-specific primer pair away from the double stranded product to generate a plurality of amplified target sequences.

In some embodiments, the amplified target sequences may be ligated to one or more adaptors. In some embodiments, the adaptors may include one or more DNA barcodes or tagging sequences. In some embodiments, the amplified target sequences once ligated to an adaptor may undergo a nick translation reaction and/or further amplification to generate a library of adaptor-ligated amplified target sequences. Exemplary methods of multiplex amplification are described in U.S. Patent Application Publication No. 2012/0295819 A1, published on Nov. 22, 2012 (U.S. application Ser. No. 13/458,739, filed on Apr. 27, 2012), and titled "Methods and Compositions for Multiplex PCR."

In various embodiments, the method of performing multiplex PCR amplification may include contacting a plurality of target-specific primer pairs having a forward and reverse primer, with a population of target sequences to form a plurality of template/primer duplexes; adding a DNA polymerase and a mixture of dNTPs to the plurality of template/primer duplexes for sufficient time and at sufficient temperature to extend either (or both) the forward or reverse primer in each target-specific primer pair via template-dependent synthesis thereby generating a plurality of extended primer product/template duplexes; denaturing the extended primer product/template duplexes; annealing to the extended primer product the complementary primer from the target-specific primer pair; and extending the annealed primer in the presence of a DNA polymerase and dNTPs to form a plurality of target-specific double-stranded nucleic acid molecules.

Adaptor-Joining Methods:

In some embodiments of the present disclosure, methods for preparing a library of polynucleotide constructs may include an adaptor-joining step. In some embodiments, a plurality of polynucleotide fragments may include at least two polynucleotide fragments that are joined to one or more nucleic acid adaptors by hybridization (e.g., with or without a primer extension reaction) or enzymatic ligation (e.g., a ligase reaction) to generate adaptor-fragment constructs. In some embodiments, one end or both ends of polynucleotide fragments may be joined to at least one type of nucleic acid adaptor. One or both ends of a polynucleotide fragment can be joined to at least one nucleic acid adaptor, including barcoded adaptors, sequencing primer adaptors, amplification primer adaptors, universal adaptors, blocking oligonucleotide adaptors, and/or others.

In some embodiments, a nucleic acid adaptor may include nucleotide sequences that are complementary to sequencing primers (e.g., P1, P2, and/or A), amplification primers, universal sequences, and/or barcode sequences. For example, released mate pair constructs may be joined at each end to a different sequencing adaptor to prepare a nucleic acid library for sequencing with SOLiD™ sequencing reactions (as disclosed in PCT Publication No. WO 2006/084131) or sequencing with ion-sensitive sequencing reactions (e.g., Ion Torrent PGM™ and Proton™ sequencers from Life Technologies Corporation, see for example, U.S. Patent Application Publication Nos. 2010/0301398, 2010/0300895, 2010/0300559, 2010/0197507, 2010/0137143, 2009/0127589; and 2009/0026082, which are incorporated by reference in their entireties).

Barcoded Adaptor Sequences:

In some embodiments of the present disclosure, methods for preparing a library of polynucleotide constructs may include joining at least one end of a plurality of polynucleotide fragments to a nucleic acid adaptor having a barcode sequence. A barcode sequence may be a selected sequence of nucleotide bases (e.g., adenine, guanine, cytosine, thymine, uracil, inosine, and/or analogs thereof) in the polynucleotide strand that serves to identify the polynucleotide strand and/or distinguish it from other polynucleotide strands (e.g., those containing a different target sequence of interest). In some embodiments, a barcode adaptor may include a unique identification sequence (e.g., barcode sequence). A barcode sequence can be used for various purposes, such as tracking, sorting, and/or identifying the samples.

Because different barcode sequences may be associated with different polynucleotide strands, these barcode sequences may be useful in multiplexed sequencing of different samples. In some embodiments, a barcode adaptor may be used for constructing multiplex nucleic acid libraries. In some embodiments, one or more barcode sequences may allow for identification of a particular adaptor among a mixture of different adaptors having different barcodes sequences. For example, a mixture may include 2, 3, 4, 5, 6, 7-10, 10-50, 50-100, 100-200, 200-500, 500-1000, or more different adaptors having unique barcode sequences. Examples of various adaptors having barcode sequences can be found in PCT Publication No. WO 2012/044847 (PCT Application No. PCT/US2011/054053), which is incorporated by reference in its entirety.

In various high throughput DNA sequencing technologies (such as sequencing-by-synthesis), it may be desirable to permit sequencing of different samples that are pooled together for simultaneous analysis (sometimes referred to as multiplexed sequencing).

When carrying out multiplexed sequencing, it may generally be desirable to identify the origin of each sample, which may require that the sequencing data be deconvolved for each sample. In particular, it may be desirable to uniquely identify the source of the sequence data derived from a multiplex sample (for example, to identify a particular nucleic acid species associated with different sample populations). One approach to facilitate sample identification may be the use of unique nucleic acid identifier sequences (barcode adaptors) that are embedded within the sample construct so that sequencing data can be correctly identified or associated with its source sample.

Computer-Implement System:

FIG. 1 depicts a block diagram that illustrates a computer system 100, upon which embodiments of the present teachings may be implemented. In various embodiments, computer system 100 may include a bus 102 and/or other communication mechanism for communicating information, and a processor 104 coupled with bus 102 for processing information. In various embodiments, computer system 100 may also include a memory 106, which can be a random access memory ("RAM") and/or other dynamic storage device, coupled to bus 102 for determining base calls, and instructions to be executed by processor 104. Memory 106 may also be used for storing temporary variables or other intermediate information during execution of instructions to be executed by processor 104. In various embodiments, computer system 100 may further include a read only memory ("ROM") 108 and/or other static storage device coupled to bus 102 for storing static information and instructions for processor 104. A storage device 110, such as a magnetic disk or optical disk, may be provided and coupled to bus 102 for storing information and instructions.

In various embodiments, processor 104 may include a plurality of logic gates. The logic gates can include AND gates, OR gates, NOT gates, NAND gates, NOR gates, EXOR gates, EXNOR gates, or any combination thereof. An AND gate may produce a high output only if all the inputs are high. An OR gate may produce a high output if one or more of the inputs are high. A NOT gate may produce an inverted version of the input as an output, such as outputting a high value when the input is low. A NAND (NOT-AND) gate may produce an inverted AND output, such that the output will be high if any of the inputs are low. A NOR (NOT-OR) gate may produce an inverted OR output, such that the NOR gate output is low if any of the inputs are high. An EXOR (Exclusive-OR) gate may produce a high output if either, but not both, inputs are high. An EXNOR (Exclusive-NOR) gate may produce an inverted EXOR output, such that the output is low if either, but not both, inputs are high.

TABLE 1

Logic Gates Truth Table

| INPUTS | | OUTPUTS | | | | | | |
|---|---|---|---|---|---|---|---|---|
| A | B | NOT A | AND | NAND | OR | NOR | EXOR | EXNOR |
| 0 | 0 | 1 | 0 | 1 | 0 | 1 | 0 | 1 |
| 0 | 1 | 1 | 0 | 1 | 1 | 0 | 1 | 0 |
| 1 | 0 | 0 | 0 | 1 | 1 | 0 | 1 | 0 |
| 1 | 1 | 0 | 1 | 0 | 1 | 0 | 0 | 1 |

One of skill in the art would appreciate that the logic gates may be used in various combinations to perform comparisons, arithmetic operations, and the like. Further, one of skill in the art would appreciate how to sequence the use of various combinations of logic gates to perform complex processes, such as the processes described herein.

In an example, a 1-bit binary comparison may be performed using a XNOR gate since the result is high only when the two inputs are the same. A comparison of two multi-bit values can be performed by using multiple XNOR gates to compare each pair of bits, and the combining the output of the XNOR gates using AND gates, such that the result may be true only when each pair of bits has the same value. If any pair of bits does not have the same value, the result of the corresponding XNOR gate may be low, and the output of the AND gate receiving the low input may be low.

In another example, a 1-bit adder may be implemented using a combination of AND gates and XOR gates. Specifically, the 1-bit adder may receive three inputs, the two bits to be added (A and B) and a carry bit (Cin), and two outputs, the sum (S) and a carry out bit (Gout). The Cin bit may be set to 0 for addition of two one bit values, or may be used to couple multiple 1-bit adders together to add two multi-bit values by receiving the Cout from a lower order adder. In an exemplary embodiment, S may be implemented by applying the A and B inputs to a XOR gate, and then applying the result and Cin to another XOR gate. Cout may be implemented by applying the A and B inputs to an AND gate, the result of the A-B XOR from the SUM and the Cin to another AND, and applying the input of the AND gates to a XOR gate.

TABLE 2

1-bit Adder Truth Table

| INPUTS | | | OUTPUTS | |
|---|---|---|---|---|
| A | B | Cin | S | Cout |
| 0 | 0 | 0 | 0 | 0 |
| 1 | 0 | 0 | 0 | 1 |
| 0 | 1 | 0 | 0 | 1 |
| 1 | 1 | 0 | 1 | 0 |
| 0 | 0 | 1 | 0 | 1 |
| 1 | 0 | 1 | 1 | 0 |
| 0 | 1 | 1 | 1 | 0 |
| 1 | 1 | 1 | 1 | 1 |

In various embodiments, computer system 100 may be coupled via bus 102 to a display 112, such as a cathode ray tube ("CRT") or liquid crystal display ("LCD"), for displaying information to a computer user. An input device 114, including alphanumeric and other keys, may be coupled to bus 102 for communicating information and command selections to processor 104. Another type of user input device may be a cursor control 116, such as a mouse, a trackball or cursor direction keys for communicating direction information and command selections to processor 104 and for controlling cursor movement on display 112. This input device may have two degrees of freedom in two axes, a first axis (i.e., x) and a second axis (i.e., y), that allows the device to specify positions in a plane.

A computer system 100 may perform the present teachings. Consistent with certain implementations of the present teachings, results may be provided by computer system 100 in response to processor 104 executing one or more sequences of one or more instructions contained in memory 106. Such instructions may be read into memory 106 from another computer-readable medium, such as storage device 110. Execution of the sequences of instructions contained in memory 106 may cause processor 104 to perform the processes described herein. In various embodiments, instructions in the memory may sequence the use of various combinations of logic gates available within the processor to perform the processes describe herein. Alternatively hard-wired circuitry may be used in place of or in combination with software instructions to implement the present teachings. In various embodiments, the hard-wired circuitry may include the necessary logic gates, operated in the necessary sequence to perform the processes described herein. Thus, implementations of the present disclosure are not limited to any specific combination of hardware circuitry and software.

The term "computer-readable medium" as used herein refers to any media that participates in providing instructions to processor 104 for execution. Such a medium may take many forms, including but not limited to, non-volatile media, volatile media, and transmission media. Examples of non-volatile media may include, but are not limited to, FLASH, optical, and/or magnetic disks, such as storage device 110. Examples of volatile media may include, but are not limited to, dynamic memory, such as memory 106. Examples of transmission media may include, but are not limited to, coaxial cables, copper wire, and fiber optics, including the wires that comprise bus 102.

Common forms of non-transitory computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, or any other tangible medium from which a computer may read.

In accordance with various embodiments, instructions configured to be executed by a processor to perform a method may be stored on a computer-readable medium. The computer-readable medium may be a device that stores digital information. For example, a computer-readable medium may include a compact disc read-only memory (CD-ROM) as is known in the art for storing software. The computer-readable medium may be accessed by a processor suitable for executing instructions configured to be executed.

Nucleic Acid Sequencing Platforms:

Nucleic acid sequence data may be generated using various techniques, platforms and/or technologies, including, but not limited to: capillary electrophoresis, microarrays, ligation-based systems, polymerase-based systems, hybridization-based systems, direct or indirect nucleotide identification systems, pyrosequencing, ion- or pH-based detection systems, electronic signature-based systems, etc.

Figure 2:
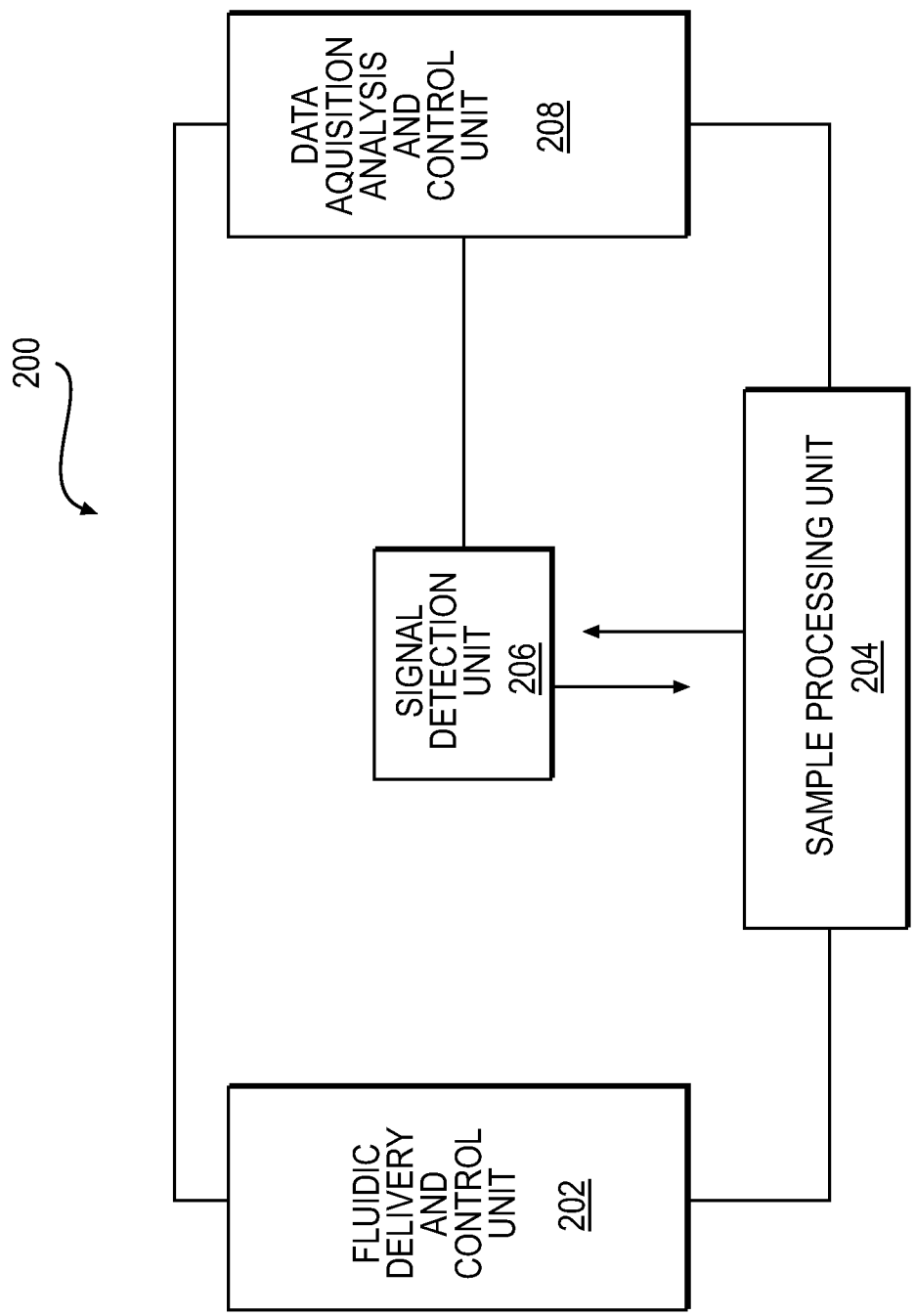
FIG. 2 depicts a schematic diagram of an exemplary system for determining a nucleic acid sequence, in accordance with various embodiments of the present disclosure.

Various embodiments of nucleic acid sequencing platforms, such as a nucleic acid sequencer, may include components as displayed in the block diagram of FIG. 2. According to various embodiments, sequencing instrument 200 may include a fluidic delivery and control unit 202, a sample processing unit 204, a signal detection unit 206, and a data acquisition, analysis, and control unit 208. Various embodiments of instrumentation, reagents, libraries, and methods used for next generation sequencing are described in U.S. Patent Application Publication No. 2009/0127589 and No. 2009/0026082, which are incorporated herein by reference. Various embodiments of instrument 200 may provide for automated sequencing that can be used to gather sequence information from a plurality of sequences in parallel, such as substantially simultaneously.

In various embodiments, the fluidic delivery and control unit 202 may include a reagent delivery system. The reagent delivery system may include a reagent reservoir for the storage of various reagents. The reagents can include RNA-based primers, forward/reverse DNA primers, oligonucleotide mixtures for ligation sequencing, nucleotide mixtures for sequencing-by-synthesis, optional ECC oligonucleotide mixtures, buffers, wash reagents, blocking reagent, stripping reagents, and the like. Additionally, the reagent delivery system may include a pipetting system and/or a continuous flow system which connects the sample processing unit with the reagent reservoir.

In various embodiments, the sample processing unit 204 may include a sample chamber, such as flow cell, a substrate, a micro-array, a multi-well tray, or the like. The sample processing unit 204 may include multiple lanes, multiple channels, multiple wells, and/or other means of processing multiple sample sets substantially simultaneously. Additionally, the sample processing unit may include multiple sample chambers to enable processing of multiple runs simultaneously. In particular embodiments, the system may perform signal detection on one sample chamber while substantially simultaneously processing another sample chamber. Additionally, the sample processing unit may include an automation system for moving or manipulating the sample chamber.

In various embodiments, the signal detection unit 206 may include an imaging and/or detection sensor. For example, the imaging and/or detection sensor may include a charge-coupled device ("CCD"), a complementary metal-oxide semiconductor ("CMOS"), an ion or chemical sensor, such as an ion sensitive layer overlying a CMOS and/or field-effect transistor ("FET"), a current and/or voltage detector, or the like. The signal detection unit 206 may include an excitation system to cause a probe, such as a fluorescent dye, to emit a signal. The excitation system may include an illumination source, such as arc lamp, a laser, a light emitting diode ("LED"), or the like. In particular embodiments, the signal detection unit 206 may include optics for the transmission of light from an illumination source to the sample and/or from the sample to the imaging and/or detection sensor. Alternatively, the signal detection unit 206 may provide for electronic and/or non-photon based methods for detection and consequently not include an illumination source. In various embodiments, electronic-based signal detection may occur when a detectable signal and/or species is produced during a sequencing reaction. For example, a signal may be produced by the interaction of a released byproduct or moiety, such as a released ion, such as a hydrogen ion, interacting with an ion or chemical sensitive layer. In other embodiments a detectable signal may arise as a result of an enzymatic cascade such as used in pyrosequencing (see, for example, U.S. Patent Application Publication No. 2009/0325145, the entirety of which being incorporated herein by reference) where pyrophosphate is generated through base incorporation by a polymerase, which further reacts with ATP sulfurylase to generate ATP in the presence of adenosine 5' phosphosulfate, wherein the ATP generated may be consumed in a luciferase mediated reaction to generate a chemiluminescent signal. In another example, changes in an electrical current may be detected as a nucleic acid passes through a nanopore without the need for an illumination source.

In various embodiments, a data acquisition, analysis, and control unit 208 may monitor various system parameters. The system parameters may include temperature of various portions of instrument 200, such as sample processing unit and/or reagent reservoirs, volumes of various reagents, the status of various system subcomponents, such as a manipulator, a stepper motor, a pump, or the like, or any combination thereof.

It will be appreciated by one skilled in the art that various embodiments of instrument 200 may be used to practice a variety of sequencing methods including ligation-based methods, sequencing by synthesis, single molecule methods, nanopore sequencing, and other sequencing techniques.

In various embodiments, the sequencing instrument 200 may determine the sequence of a nucleic acid, such as a polynucleotide and/or an oligonucleotide. The nucleic acid may include DNA and/or RNA, and may be single stranded, such as ssDNA and/or RNA, or double stranded, such as dsDNA and/or a RNA/cDNA pair. In various embodiments, the nucleic acid may include and/or be derived from a fragment library, a mate pair library, a chromatin immunoprecipitation ("ChIP") fragment, or the like. In particular embodiments, the sequencing instrument 200 may obtain the sequence information from a single nucleic acid molecule and/or from a group of substantially identical nucleic acid molecules.

In various embodiments, sequencing instrument 200 may output nucleic acid sequencing read data in a variety of different output data file types/formats, including, but not limited to: *.bam, *.fasta, *.csfasta, *seq.txt, *qseq.txt, *.fastq, *.sff, *prb.txt, *.sms, *srs and/or *.qv.

Figure 3:
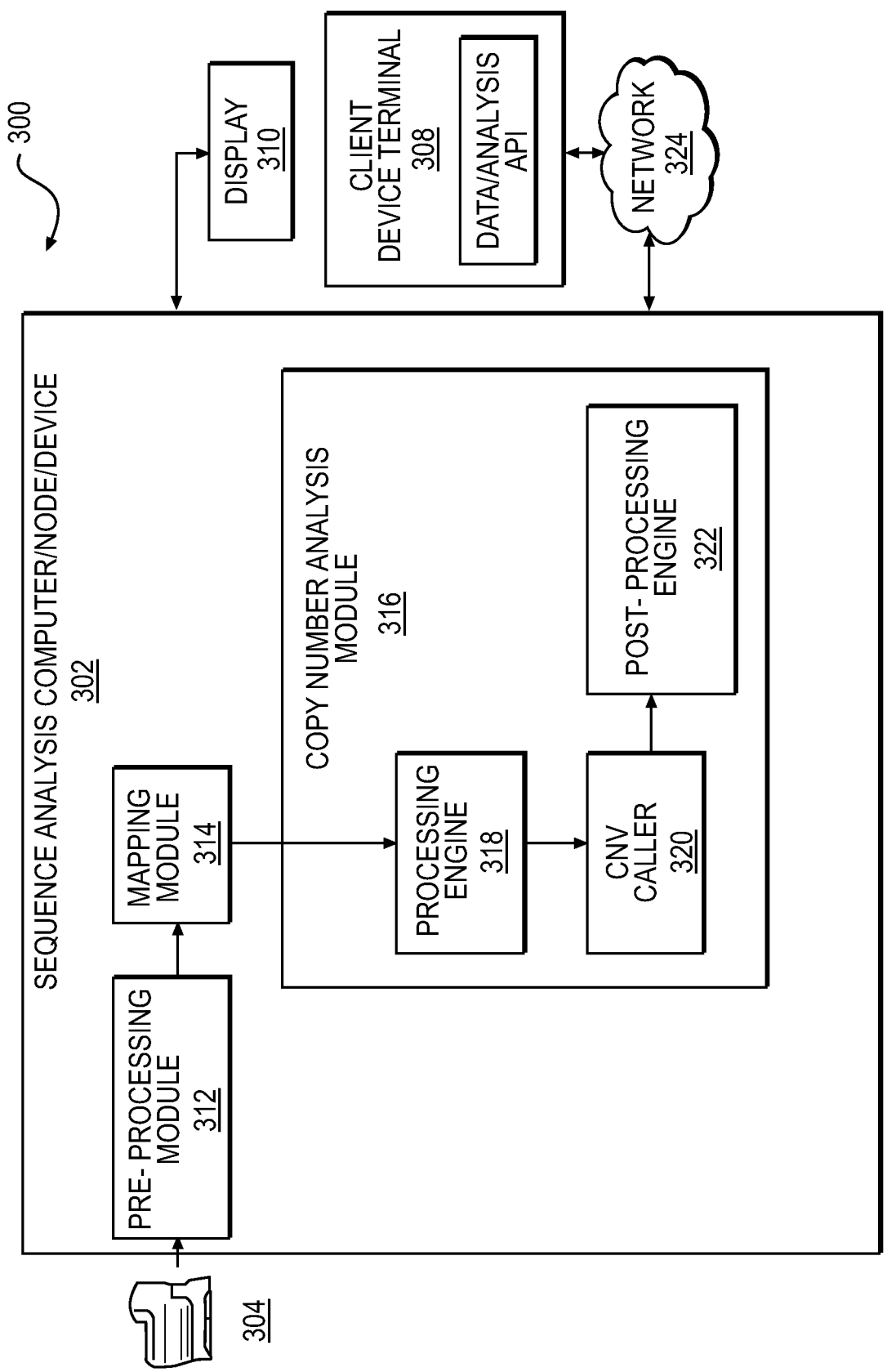
FIG. 3 depicts a schematic diagram of an exemplary genetic analysis system, in accordance with various embodiments of the present disclosure.

Methods, Systems, and Computer-Readable Media for Identifying Sequence Variation:

FIG. 3 depicts a schematic diagram of a system for identifying variants, in accordance with various embodiments. As depicted herein, variant analysis system 300 may include a nucleic acid sequence analysis device 304 (e.g., nucleic acid sequencer, real-time/digital/quantitative PCR instrument, microarray scanner, etc.), a sequence analytics computer server/node/device 302, and a display 310. The variant analysis system 300 may also include a client device terminal 308.

In various embodiments, the sequence analytics computer server/node/device 302 may be communicatively connected to the nucleic acid sequence analysis device 304, and the client device terminal 308 may be communicatively connected to the sequence analytics computer server/node/device 302 via a network connection 324 that can be either a "hardwired" physical network connection (e.g., Internet, local area network ("LAN"), wide area network ("WAN"), virtual private network ("VPN"), etc.) and/or a wireless network connection (e.g., Wi-Fi, wireless local area network ("WLAN"), etc.).

In various embodiments, the sequence analytics computer server/node/device 302 may be a workstation, mainframe computer, distributed computing node (such as, part of a "cloud computing" and/or distributed networking system), personal computer, mobile device, etc. In various embodiments, the nucleic acid sequence analysis device 304 may be a nucleic acid sequencer, real-time/digital/quantitative PCR instrument, microarray scanner, etc. It should be understood, however, that the nucleic acid sequence analysis device 304 may essentially be any type of instrument that can generate nucleic acid sequence data from samples obtained from an individual.

The sequence analytics computing server/node/device 302 may be configured to host an optional pre-processing module 312, a mapping module 314, and a copy number analysis module 316.

The pre-processing module 312 may be configured to receive from the nucleic acid sequence analysis device 304 and perform processing steps, such as conversion from color space to base space or from flow space to base space, determining call quality values, preparing the read data for use by the mapping module 314, and the like.

The mapping module 314 may be configured to align (i.e., map) a nucleic acid sequence read to a reference sequence. Generally, the length of the sequence read may be substantially less than the length of the reference sequence. In reference sequence mapping/alignment, sequence reads may be assembled against an existing backbone sequence (e.g., reference sequence, etc.) to build a sequence that is similar but not necessarily identical to the backbone sequence. Once a backbone sequence is found for an organism, comparative sequencing or re-sequencing may be used to characterize the genetic diversity within the organism's species or between closely related species. In various embodiments, the reference sequence may be a whole/partial genome, whole/partial exome, etc.

In various embodiments, the sequence read and reference sequence may be represented as a sequence of nucleotide base symbols in base space. In various embodiments, the sequence read and reference sequence may be represented as one or more colors in a color space. In various embodiments, the sequence read and reference sequence may be represented as nucleotide base symbols with signal and/or numerical quantitation components in flow space.

In various embodiments, the alignment of the sequence fragment and reference sequence may include a limited number of mismatches between the bases that comprise the sequence fragment and the bases that comprise the reference sequence. Generally, the sequence fragment may be aligned to a portion of the reference sequence in order to minimize the number of mismatches between the sequence fragment and the reference sequence.

The copy number analysis module 316 may include a processing engine 318, a copy number variant caller 320, and an optional post-processing engine 322. In various embodiments, copy number analysis module 316 may be in communications with the mapping module 314, and may request and receive data and information (through, e.g., data streams, data files, text files, etc.) from mapping module 314.

The processing engine 318 may be configured to receive mapped reads from the mapping module 314, determine coverages for target regions of the genome (tiles, ampliseq panels may have overlapping targets, which may be mapped to each amplicon target), and/or normalize the tile coverages based on average and/or mode of the coverage across the tiles and the GC content. Additionally, the processing engine 318 may be configured to correct for batch effects. In various embodiments, the processing engine 318 may determine the normalized coverages for both a sample and/or a control.

The copy number variation ("CNV") caller 320 may be configured to receive the normalized coverages from the processing engine 318, determine scores, such as likelihoods, for an amplicon to be present in various ploidy states, determine a maximum score path through the ploidy states across the amplicons, and calculate score ratios, such as log likelihood ratios, of the maximum score path to the expected ploidy state and the closest scoring neighboring ploidy state. Additionally, the CNV caller 320 may identify copy number variants based on the maximum score ploidy states that can overcome a preset ploidy transition penalty. The transition penalty may be adjusted to accomplish desired sensitivity or specificity of the algorithm.

The post-processing engine 322 may be configured to receive the copy number variants and the log likelihood ratios determined by the CNV caller 320 and perform additional processing steps, such as filtering copy number variants, and formatting the read data for display on display 310 and/or use by client device terminal 308.

The client device terminal 308 may be a thin client or thick client computing device. In various embodiments, client device terminal 308 may have a web browser (e.g., Chrome, Internet Explorer, Firefox, Safari, etc.) that may be used to communicate information to and/or control the operation of the pre-processing module 312, mapping module 314, processing engine 318, CNV caller 320, and post-processing engine 322 using the web browser to control their function. For example, the client device terminal 308 may be used to configure the operating parameters (e.g., match scoring parameters, annotations parameters, filtering parameters, data security and retention parameters, etc.) of the various modules, depending on the requirements of the particular application. Similarly, client device terminal 308 may also be configured to display the results of the analysis performed by the copy number analysis module 316 and the nucleic acid sequence analysis device 304.

It should be understood that the various data stores disclosed as part of variant analysis system 300 may be represented as hardware-based storage devices (e.g., hard drive, flash memory, RAM, ROM, network attached storage, etc.) and/or instantiations of a database stored on a stand-alone and/or networked computing device(s).

It should also be appreciated that the various data stores and modules/engines shown as being part of the variant analysis system 300 may be combined or collapsed into a single module/engine/data store, depending on the requirements of the particular application or system architecture. Moreover, in various embodiments, the variant analysis system 300 may comprise additional modules, engines, components or data stores as needed by the particular application or system architecture.

In various embodiments, the variant analysis system 300 may be configured to process the nucleic acid reads in color space. In various embodiments, variant analysis system 300 may be configured to process the nucleic acid reads in base space. In various embodiments, variant analysis system 300 may be configured to process the nucleic acid sequence reads in flow space. It should be understood, however, that the variant analysis system 300 disclosed herein may process or analyze nucleic acid sequence data in any schema or format as long as the schema or format may convey the base identity and position of the nucleic acid sequence.

Batch Effect Detection and Correction:

As discussed above, batch effects may be detected and corrected using principal components analysis ("PCA"). In a panel of an assay, a set of n amplicons may be arranged in genomic order, and the set of n amplicons may represent genomic locations that are diploid in normal samples. Then, without taking into consideration sample specific effects, such as guanine-cytosine bias ("GC bias") and/or length bias, per amplicon efficiency in polymerase chain reaction ("PCR") may label n different amplicons in a panel by indices i=1, 2, . . . , n. An amplicon "I" property may be represented by A=($a_1$, $a_2$, . . . , $a_n$), $\Sigma a_i$=1. The samples may have equimolar DNA input for these amplicons. Thus, an expected number of reads for final amplification for amplicon j may be proportional to $a_j$. $a_j$ may be estimated by combining a set of K samples where all amplicons have known and identical per amplicon CN. Combining, for estimating $a_j$, may be at function, such as mean, median, trimmed mean, etc. For example, using mean as the combining function for $a_j$, $a_j$ would equal the sum of the reads for an amplicon j in a sample k divided by the sum of the total readings in the sample k. Thus, the formula for the commingling function using mean may be represented by the formula:

$$a_j = \frac{\sum_k r_{j,k}}{\sum_k R_k} Rk,$$

where $r_{j,k}$ represents the reads for amplicon j in sample k, and $R_k$ is the total reads in sample k.

A sample may not be uniformly diploid with reads per amplicon, and may be expressed as ($r_1$, $r_2$, . . . , $r_n$), where r is a read per amplicon and n is an integer. The sum of the reads per amplicon may be R, and expressed as $\Sigma r_i$=R. Copy number values per amplicon may be expressed as a vector C, which is ($c_1$, $c_2$, . . . , $c_n$), where c is a copy number value for amplicon "i".

$\bar{c}$ may be an average ploidy across a panel of an array. For a germline sample with amplicons on the autosomes, $\bar{c}$ may be close to 2. In a tumor sample, $\bar{c}$ may not be close to 2. A multiplicative bias 2/$\bar{c}$ may be a constant for all amplicons in the tumor sample.

A mean $\bar{c}$ may satisfy $r_i/R = c_i a_i/\bar{c} + \varepsilon$, where $\varepsilon$ is an error that may be expected to have a mean close to 0 for large $r_i$ and large R. Rewriting the above formula with the error being ignored allows for an estimate $c_i$ to be determined, shown in the following formula:

$$c_i = (r_i/R) * \bar{c}/a_i \quad (1)$$

Rewriting formula (1) above into logarithms, may result in the following formula:

$$\log c_i = \log r_i/R + \log \bar{c} - \log a_i \quad (2)$$

In formula (2), a copy number per amplicon may be estimated by the ratio of the reads to the total adjusted reads per amplicon efficiency and sample ploidy. A multiplicative batch effect that perturbs the amplicon efficiency may be assumed. The multiplicative batch effect may be represented as vector B, where B=($b_1$, $b_2$, . . . , $b_n$) and n is an integer. The multiplicative batch effect that perturbs the amplicon efficiency may be assumed multiplicative in deference to likely chemistry.

Some samples may have amplicons with few reads, e.g., the copy number is close to 0 or a failure to amplify. Amplicons in such samples may be treated separately, as the multiplicative effects model may not be appropriate.

Assuming there are k=1, 2, . . . , K samples may include some component of this effect. Sample k may have a logarithmic amplification efficiency represented to vector (log A+$\alpha_k$ log B). These samples need not be uniformly diploid. Taking into account k, formula (2) may be rewritten as:

$$\log c_{i,k} = \log r_{i,k}/R + \log \bar{c} - \log a_i - \alpha_k \log b_i \quad (3)$$

With no loss of generality, B may be replaced by B/$b_1$'s. $C_k$ may be a sample specific constant given by log $\bar{c} - \alpha_k$ log $b_1$. Accordingly, formula (3) may be rewritten as:

$$\log c_{i,k} = \log r_{i,k}/R + C_k - \log a_i - \alpha_k \log b_i \quad (4)$$

Rearranging formula (4), may be as follows:

$$\log r_{i,k}/R - \log a_i = \log c_{i,k} - C_k + \alpha_k \log b_i \quad (5)$$

The left side of formula (5) may be known from observation and estimates, and the right side of formula (5) may require estimation. Reformulating formula (5) may provide K n-dimensional observations, as shown in the following formula:

$$Y_k = \log(C) + \alpha_k \log B - C_k \quad (6)$$

Where, for a sample k, $Y_{i,k} = \log r_{i,k}/R - \log a_i$, vector $Y_k = [Y_{1,k}, Y_{2,k}, \ldots, Y_{n,k}]$, vector log (C)=[log $c_{1,k}$, log $c_{2,k}$, . . . , log $c_{n,k}$], for i=1, . . . , n, and where n is an integer.

The copy number values at adjacent genomic positions are likely the same for panels where there are multiple amplicons per gene, and thus, may be used.

Letting log $B_1$=(log $b_1$, . . . , log $b_{n-1}$) and log $B_2$=(log $b_2$, . . . , log $b_n$), where n is an integer, and using similar notations for $Y_{1,k}$, $Y_{2,k}$, $C_{1,k}$, $C_{2,k}$, etc., then $$\log C_{2,k} - \log C_{1,k} \approx 0 \quad (7)$$

may yield:

$$Y_{2,k} - Y_{1,k} \approx \alpha_k (\log B_{2,k} - \log B_{1,k}) \quad (8)$$

To estimate $\hat{\beta} = \log B_{2,k} - \log B_{1,k}$ and $\hat{\alpha}_k$ for each sample, principal components analysis ("PCA") may be used. PCA may allow simultaneous estimation of multiple such batch effects that operate independently but jointly affect a sample. Each principal component represents one such batch effect B. To recover the original log B, the following linear equations may be used:

$$0 = \log b_1 \quad (9)$$

$$\beta_i = \log b_{i+1} - \log b_i, i=2, \ldots, n \quad (10)$$

which is solvable by the partial sums of $\beta$:

$$\log \hat{b}_i = \Sigma_{j=1}^{i} \hat{\beta}_j \quad (11)$$

The final correction may be applied to remove batch effects for as many principal components as needed, as shown as follows:

$$\log \hat{c}_i = \log r_i/R + C_k - \log a_i - \hat{\alpha}_k \log \hat{b}_i \quad (12)$$

Such batch effects may be computed either using a second training set of samples with unknown copy number changes and applied on an ongoing basis to new samples, or may be computed post-hoc on a set of samples with unknown copy number changes and used to remove batch effects within this set.

Figure 4:
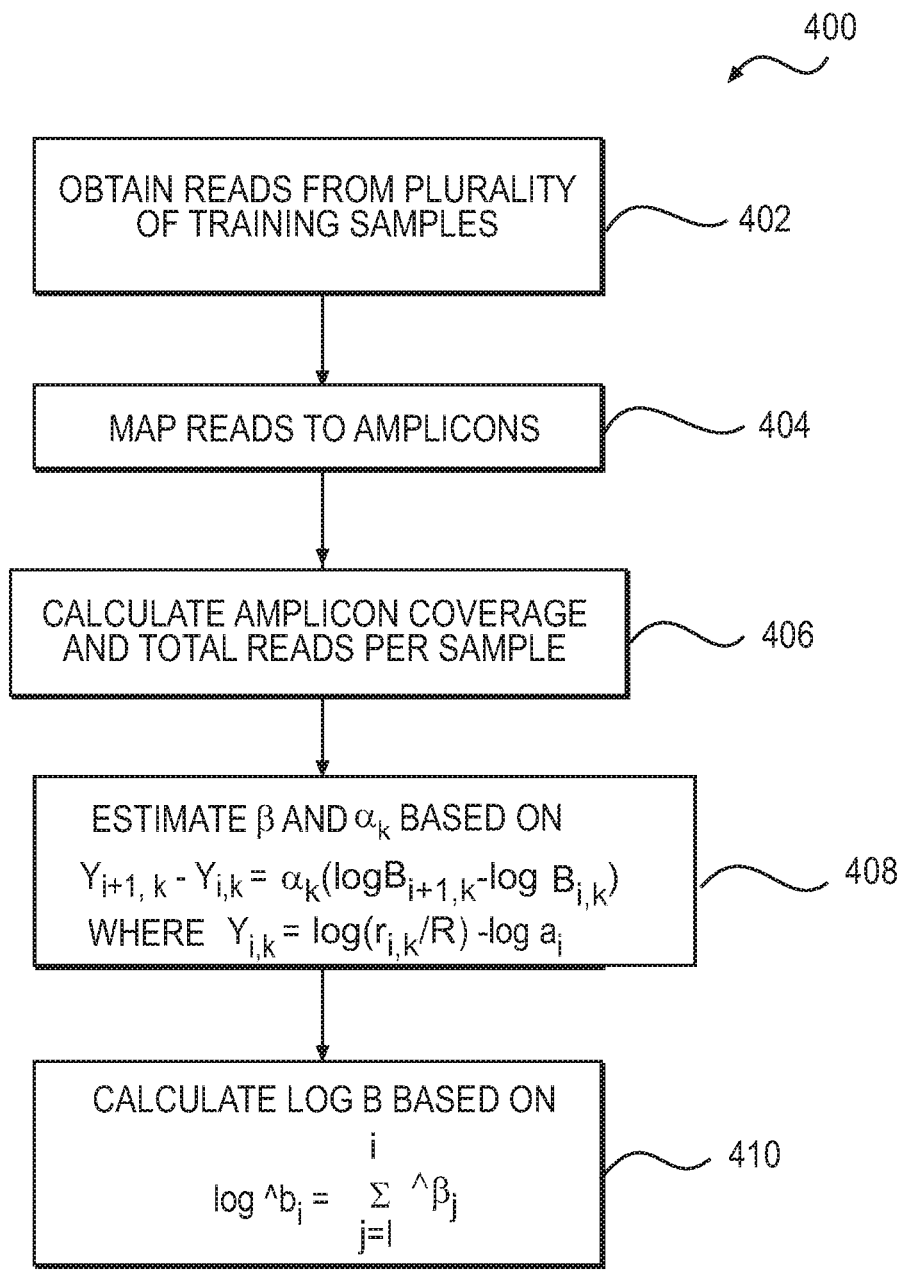
FIG. 4 depicts a flow diagram illustrating an exemplary method of determining batch effect values, in accordance with various embodiments of the present disclosure.

FIG. 4 depicts an exemplary flow diagram showing a method 400 for determining batch effects, in accordance with various embodiments. At step 402, reads from a plurality of training samples are obtained. The training samples may include a set of normal samples with a known ploidy. In various embodiments, the training samples may further include a set of non-normal samples with an unknown ploidy. In various embodiments, the nucleic acid material obtained from the training samples may be subjected to multiple amplifications to selectively amplify a plurality of genomic regions. Additionally, in various embodiments, barcoded adaptors may be added to the amplicons for at least a subset of the training samples. The amplicons may be sequenced to produce a plurality of reads for each of the normal samples.

In various embodiments, at least a portion of the sample may be prepared in different batches, such that the sample preparation for the samples involves at least one of different reagent lots, different preparers, different sample preparation equipment, and the like. Additionally, at least a portion of the samples may be analyzed at different times, on different chips, on different instruments, or the like. Ideally, the samples may be prepared in substantially the same way, such as using similar kits and protocols, and analyzed in substantially the same way, such as using similar instruments and chips.

At step 404, the reads may be mapped to a nucleic acid sequence to identify a corresponding nucleic acid region, such as mapping the reads to amplicons. At step 406, an amplicon coverage (for example, a number of reads mapped to an amplicon) and total reads (for example, a number of mapped reads) may be calculated per sample. In various embodiments, a subset of reads may be mapped to off target amplification products. Reads mapped to off target amplification products may be discarded and not included in the total reads. In various embodiments, a difference in the read counts between adjacent regions or amplicons, rather than the read counts of the individual regions or amplicons, may be used. In this way, variability in read counts due to differences in a copy number may be excluded from the principal component analysis.

At step 408, principal components analysis ("PCA") may be used to estimate $\beta$ and the scaling factor ($\alpha_k$) using formula 8, as described above. PCA may be used to determine one or more batch effects. At step 410, the batch effect (log B) may be calculated based on $\beta$. By using the formula 11 above, calculating log B may be solvable by the partial sums of $\beta$, where $\log \hat{b}_i = \Sum_{j=1}^{i} \hat{\beta}_j$.

Figure 5:
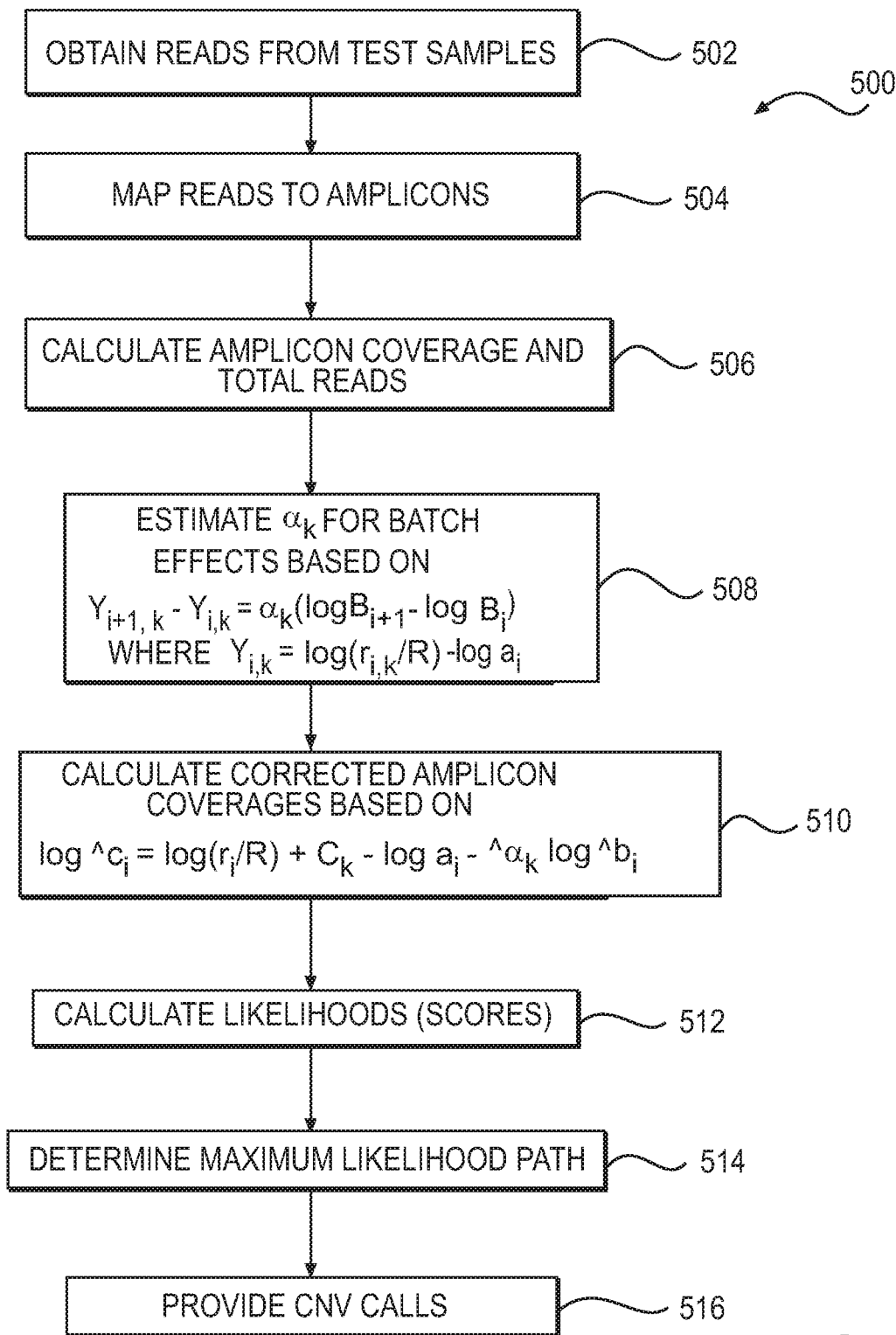
FIG. 5 depicts a flow diagram illustrating an exemplary method of identifying copy number variations, in accordance with various embodiments of the present disclosure.

FIG. 5 depicts an exemplary flow diagram showing a method 500 for identifying a copy number variation in a test sample suspected of containing chromosomal abnormalities, gene duplications, and/or gene deletions, in accordance with various embodiments. In various embodiments, the test sample may be a sample suspected of containing copy number variations in at least a portion of the genome, such as due to chromosomal abnormalities (gain and/or loss of a chromosome, or a portion thereof). In various embodiments, the test sample may include cancer cells in which gene duplications and/or gene deletions have occurred, which may cause a change in a copy number for one or more genes.

At step 502, reads from test samples may be obtained. The test samples may be samples with an unknown ploidy. In various embodiments, the test samples may be subjected to the sample preparation and analysis procedures that the normal samples were subjected to. For example, the nucleic acid material obtained from the test samples may be subjected to similar multiple amplifications to selectively amplify the plurality of genomic regions. The amplicons may be sequenced to produce a plurality of reads for the test samples. In various embodiments, barcoded adaptors may be added to the amplicons enabling multiple samples to be sequenced substantially simultaneously and the sequences from barcoded adaptor may be used to identify which read corresponds to which sample.

At step 504, the reads may be mapped to a nucleic acid sequence to identify a corresponding nucleic acid region, such as mapping the reads to a reference sequence containing nucleic acid sequences corresponding to the amplicons. At step 506, amplicon coverage (for example, a number of reads mapped to an amplicon) and total reads (for example, a number of mapped reads) may be calculated for the test samples. In various embodiments, a subset of reads can be mapped to off target amplification products. Reads mapped to off target amplification products may be discarded and not included in the total reads.

At step 508, PCA may be used to estimate the scaling factor ($\alpha_k$) using formula 8, as described above. In various embodiments, $\beta$ may be calculated previously based on a set of known samples, such as previously described. At step 510, the amplicon coverages for the test samples may be corrected to account for batch effects based on the $\alpha_k$ determined in step 508 and log $b_i$ calculated based on the known samples. In various embodiments, the total reads may be recalculated based on the corrected amplicon coverages. In step 510, the correction may be applied to remove batch effects for as many principal components as needed based on formula 12 as described above and as shown as follows: $\log \hat{c}_i = \log r_i/R + C_k - \log a_i - \hat{\alpha}_k \log \hat{b}_i$. The calculated corrected amplicon coverages may be used to determine a relative copy number.

In one embodiment, a gene level copy number confidence score may be calculated based on the calculated corrected amplicon coverages, for example, as shown in steps 512 and 514 below At step 512, a likelihood (probability) for an amplicon being in various ploidy states may be calculated. The likelihood may be a score, which may be a function and/or ad-hoc rule that discriminates between a true and other ploidy states. In various embodiments, prior to calculating a likelihood (probability), the corrected amplicon coverages may be normalized, such as based on the total reads. In various embodiments, the likelihood (score) may be calculated for a range of ploidy states, such as a range from a ploidy of 1 through 10. In an exemplary embodiment, the likelihood (score) for a ploidy state may be calculated as a likelihood using the equation L=N (S−C, 0, Sd), where S is the corrected amplicon coverage, C is a scaled baseline amplicon coverage for the amplicon in the explored ploidy state, and Sd is a standard deviation of the amplicon coverage. The standard deviation (Sd) may be made dependent on the sample and control amplicon coverage, and may be predetermined using sequencing of training sample replicates. In various embodiments, the scaled baseline coverage may be determined by scaling the normalized baseline to an explored ploidy state. For example, the normalized baseline coverage for a diploid region may be approximately 2, and when exploring a ploidy state of 3 (triploid), the normalized baseline coverage can be multiplied by 3/2, such that the scaled baseline coverage may be approximately 3. Thus, for a tile or an amplicon that is in a triploid region in the sample, the difference between the normalized sample coverage and the scaled baseline coverage may be greater when scoring a ploidy state of 2 and/or 5 than when scoring a ploidy state of three.

In various embodiments, such as when determining a copy number variation for a sample from a cancerous tumor, multiple subpopulations of cells may exist in the sample. For example, a sample from a cancer biopsy may include normal cells as well as cancerous cells, and the sample may have an effective ploidy state that represents a weighted average of the ploidy state of the normal cells and the cancerous cells. To identify copy number changes for specific genes in such a sample, scores may be calculated for none-integer ploidy states. For example, scores may be calculated over a range of values in steps of one tenth, such as 2.0, 2.1, 2.2, 2.3, etc.

At step 514, a maximum score path through a ploidy state for each tile may be determined. In various embodiments, scoring of the path may include a summation of the scores for each ploidy state along the path and a transition penalty for each pair of neighboring tiles where the ploidy state changes. The maximum score path may then be determined using a dynamic programming algorithm, such as the Viterbi algorithm in the implementations of Hidden Markov Models, the Earley algorithm, and the Needleman-Wunsch algorithm. In an exemplary embodiment, the maximum score path may be a maximum likelihood path calculated by summing the log-likelihoods of the ploidy states along the path and the transition penalty.

A transition penalty may be a deterrent to changing copy-number state for small segments, unless there is an overriding support from the state likelihoods of the tiles in the segment which may outweigh the transition penalty. In various embodiments, the transition penalty may be a function of the log of the probability that the copy-number state changes for any given random tile. Making the transition probability smaller may result in calling larger copy number variation ("CNV") segments, or segments with greater support for the changed state (i.e., a greater difference in a copy number). Therefore, the transition penalty may be adjusted to achieve a desired sensitivity and/or specificity.

The transition probability may increase for larger gaps between tiles. The gaps between tiles may arise from an un-amplified (un-sequenced) part of the genome that may be skipped in the algorithm. After a sufficiently large gap between tiles, the copy number state of the tile before the gap may have no information about the copy-number state of a tile after the gap. Therefore, the transition probability may become equal for all copy-number states after the gap. The increase to this all-equal probability may be exponential, and therefore, may be estimated by a linear increase in the log space.

In various embodiments, rather than determining a maximum likelihood path through multiple ploidy states, the copy number may be determined by averaging ratios of the normalized coverage of the sample and a baseline over a portion of the genome. For example, to detect gene duplication and/or gene deletion, the ratios may be averaged from each tile or amplicon within the gene. At step 516, copy number variation ("CNV") calls may be provided for the sample.

Exemplary Copy Number Analysis for Overexpressor of Cationic Peroxidase ("OCP"):

In an exemplary embodiment, 2530 amplicon totals in a panel were obtained including 2 polymerase chain reaction ("PCR") pools. In various embodiments, a number of technical effects may contribute to experiment-to-experiment variation in amplicon read counts, including a PCR pool, amplicon GC content, and amplicon length. Correction for the PCR pool may be achieved by normalizing pool specific amplicon read count median values. Correction for amplicon GC content and amplicon length may involve obtaining median amplicon read counts for ranges in GC content and/or amplicon length, fitting a spline with the median read counts, and scaling all read counts to the same value.

In the exemplary embodiment, various genes were targeted for copy number analysis, including 45 genes for the purpose of copy number gain, and 26 genes for the purpose of copy number loss. A goal of the copy number analysis is to determine a copy number estimate (including information about a confidence interval) for each gene.

Amplicon-based copy number analysis includes steps, as described above in regard to the various methods. Steps may include, for example, summarizing amplicon read counts, data pre-processing, comparing the processed data to a reference, and using statistical/machine learning methods to call copy numbers and/or change points.

Figure 6:
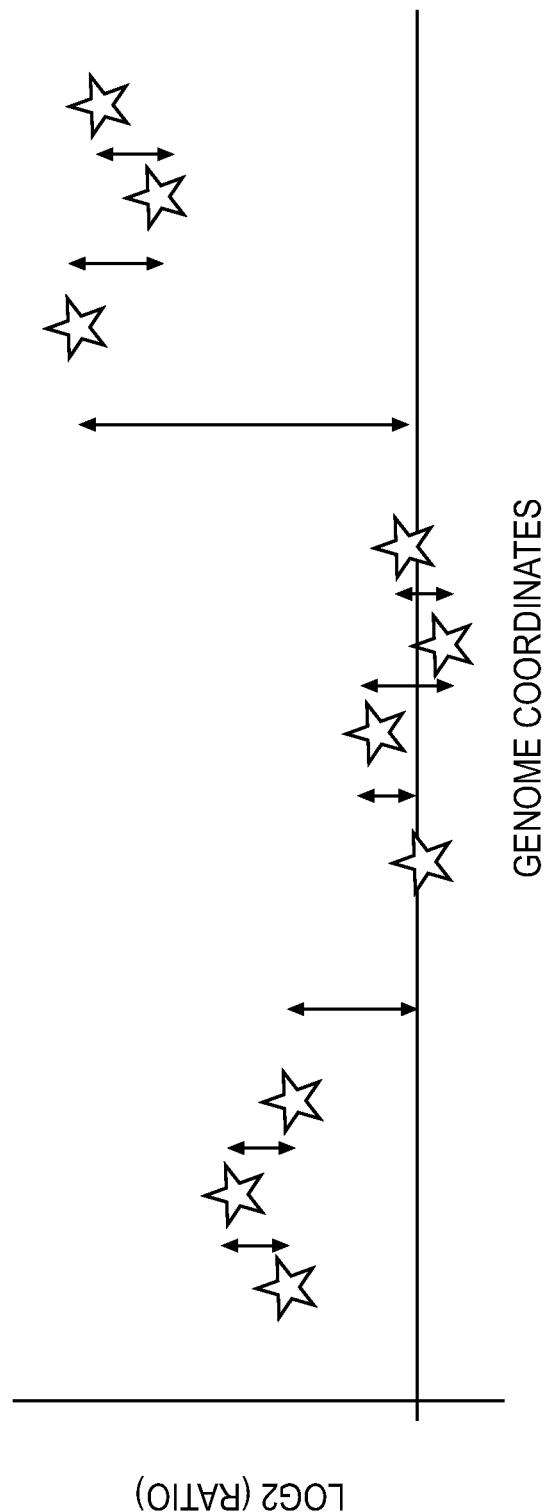
FIG. 6 depicts a graph illustrating pairwise difference lengths of genome coordinates, in accordance with various embodiments of the present disclosure.
Figure 7A:
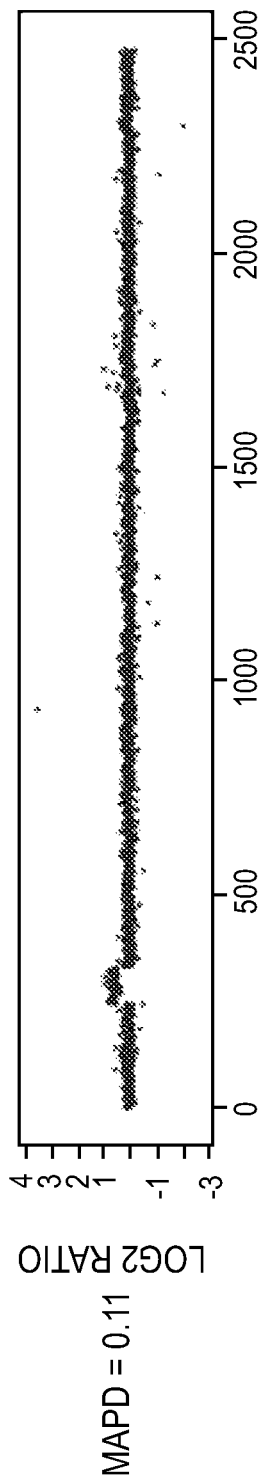
FIGS. 7A-7E depict examples of genomic data having various MAPD values, in accordance with various embodiments of the present disclosure.
Figure 7B:
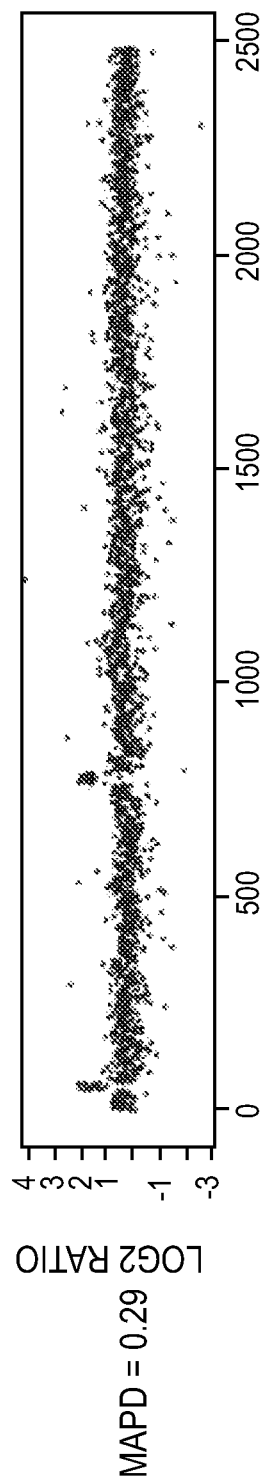
Figure 7C:
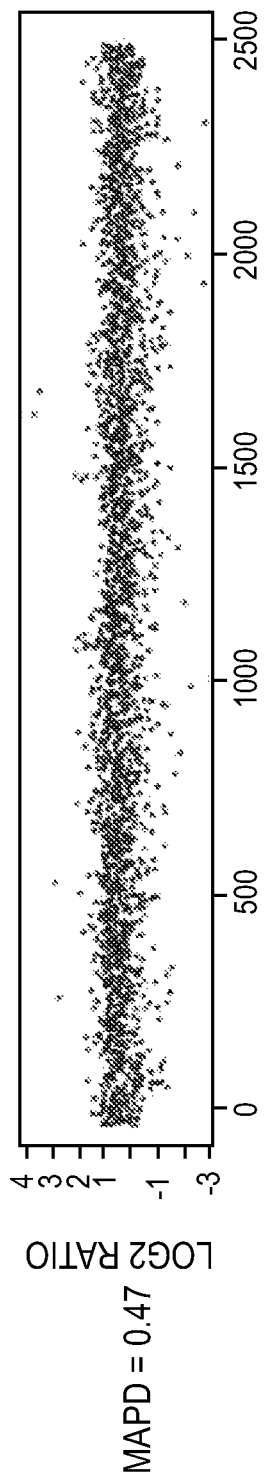
Figure 7D:
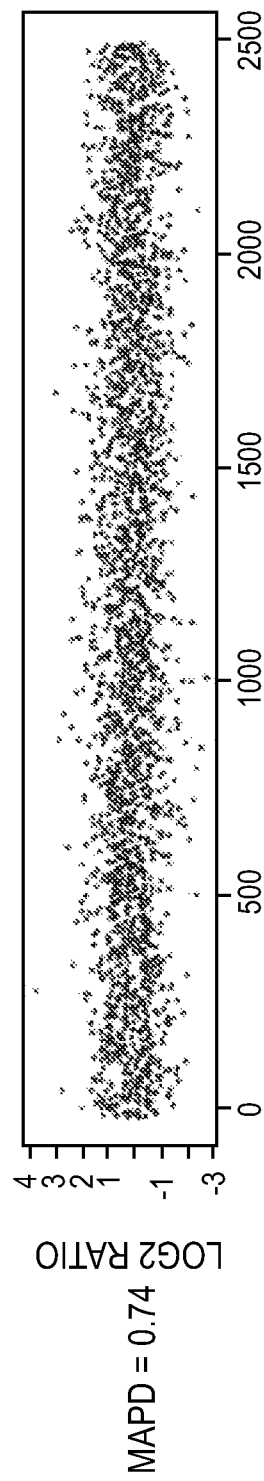
Figure 7E:
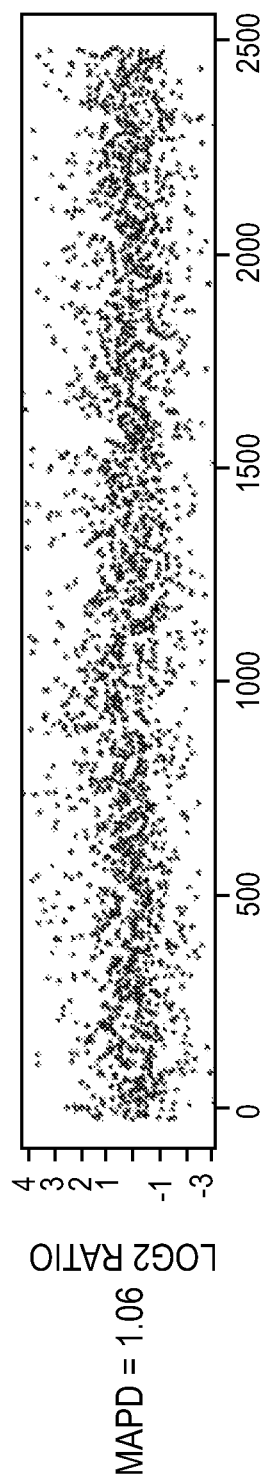

During data pre-processing, various types of data may be determined depending on how the received data compares to a reference. FIG. 6 depicts a graph illustrating pairwise difference lengths of genome coordinates, according to embodiments of the present disclosure. As shown in FIG. 6, jumps in the pairwise difference lengths may be small, and big jumps may be rare. A median absolute pairwise difference ("MAPD") may be determined based on pairwise difference lengths of genome coordinates.

FIGS. 7A-7E depict examples of genomic data having various MAPD values, according to embodiments of the present disclosure. As shown in FIGS. 7A-7E, as the MAPD value increases, the quality of genomic data decreases. In various embodiments, a poor MAPD value may be the result of significant batch effects, which may reflect systematic differences between the data being examined and the reference data. These systematic differences may negatively impact copy number analysis results. In order to reduce the impact to copy number analysis, pre-processing of sample data may be performed.

Figure 8A:
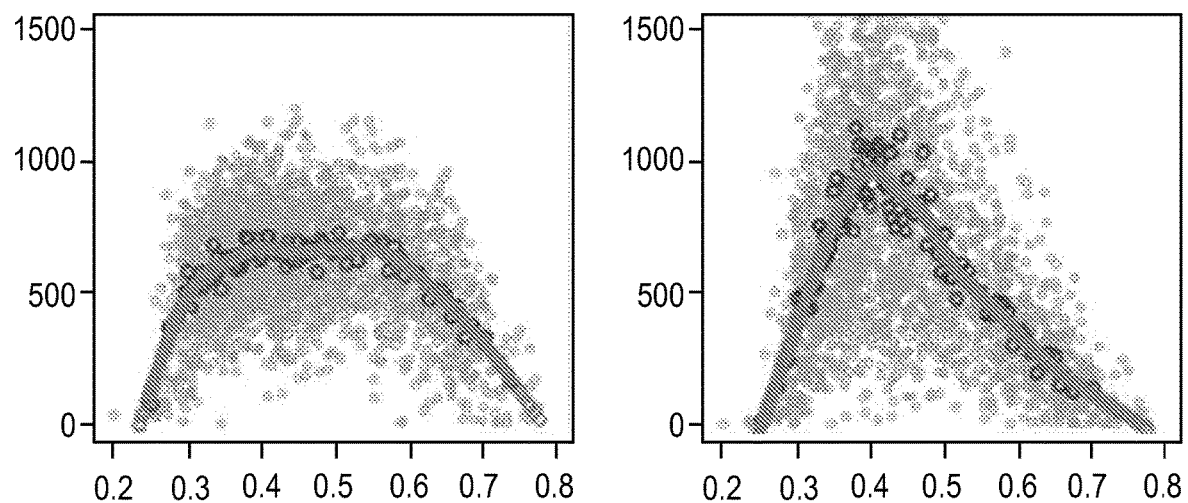
FIG. 8A depicts graphs illustrating the effect of known technical effects of GC content, in accordance with various embodiments of the present disclosure.
Figure 8B:
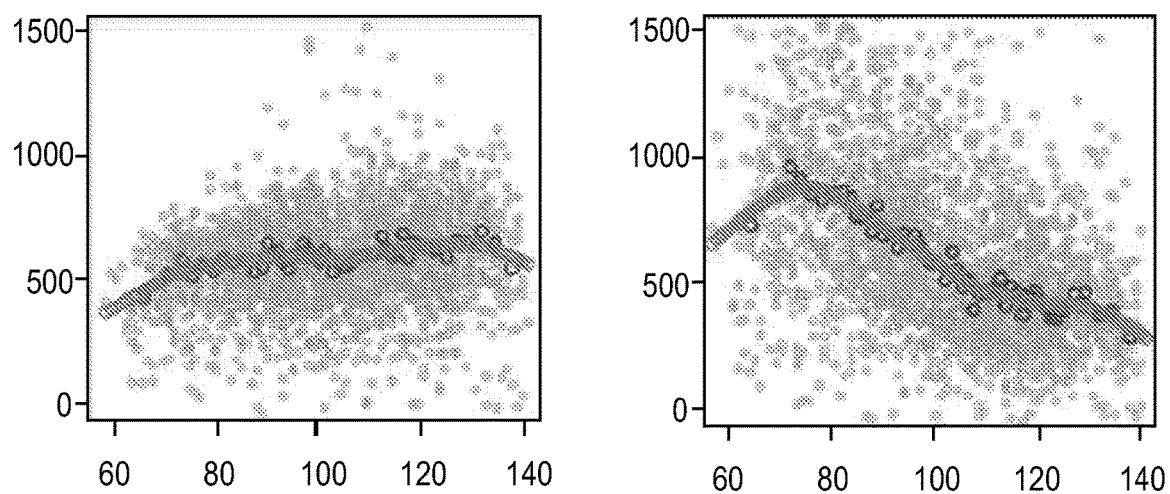
FIG. 8B depicts graphs illustrating the effect of known technical effects of amplicon length on amplicon read counts, in accordance with various embodiments of the present disclosure.

FIG. 8A depicts graphs illustrating the effect of known technical effects of GC content, and FIG. 8B depicts graphs illustrating the effect of known technical effects of amplicon length on amplicon read counts, according to embodiments of the present disclosure. For FIGS. 8A and 8B, the y-axis represents amplicon read counts after pool correction. For FIG. 8A, the x-axis represents amplicon GC fraction, and for FIG. 8B, the x-axis represents amplicon length. As shown in FIGS. 8A and 8B, the light grey data points correspond to amplicons, the dark circle data points correspond to read count median values, and the line represents the splines used for technical correction.

Figure 9:
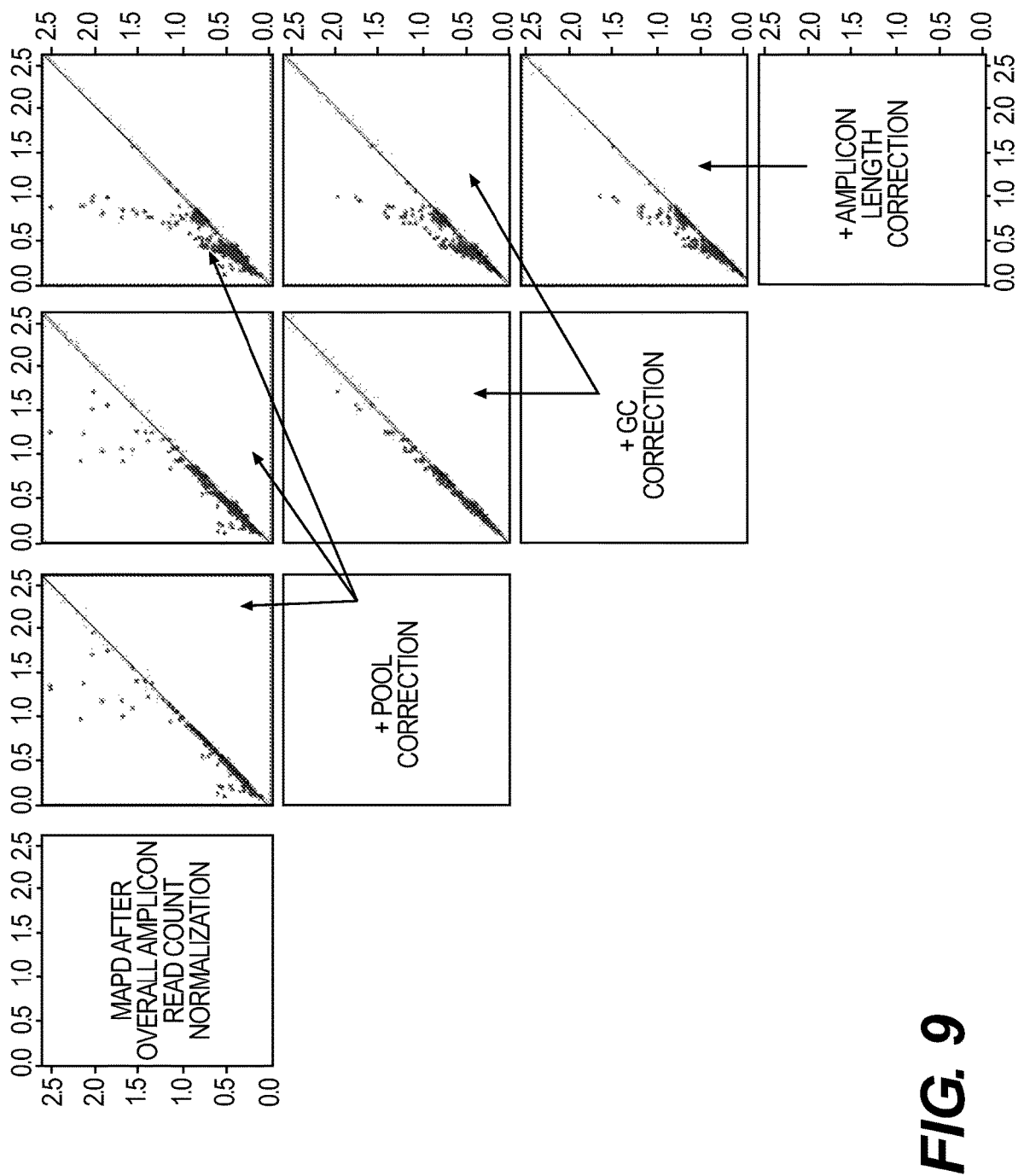
FIG. 9 depicts MAPD graphs illustrating application of the corrections for technical effects and batch effects to experiments, conducted in multiple batches, in accordance with various embodiments of the present disclosure.
Figure 10:
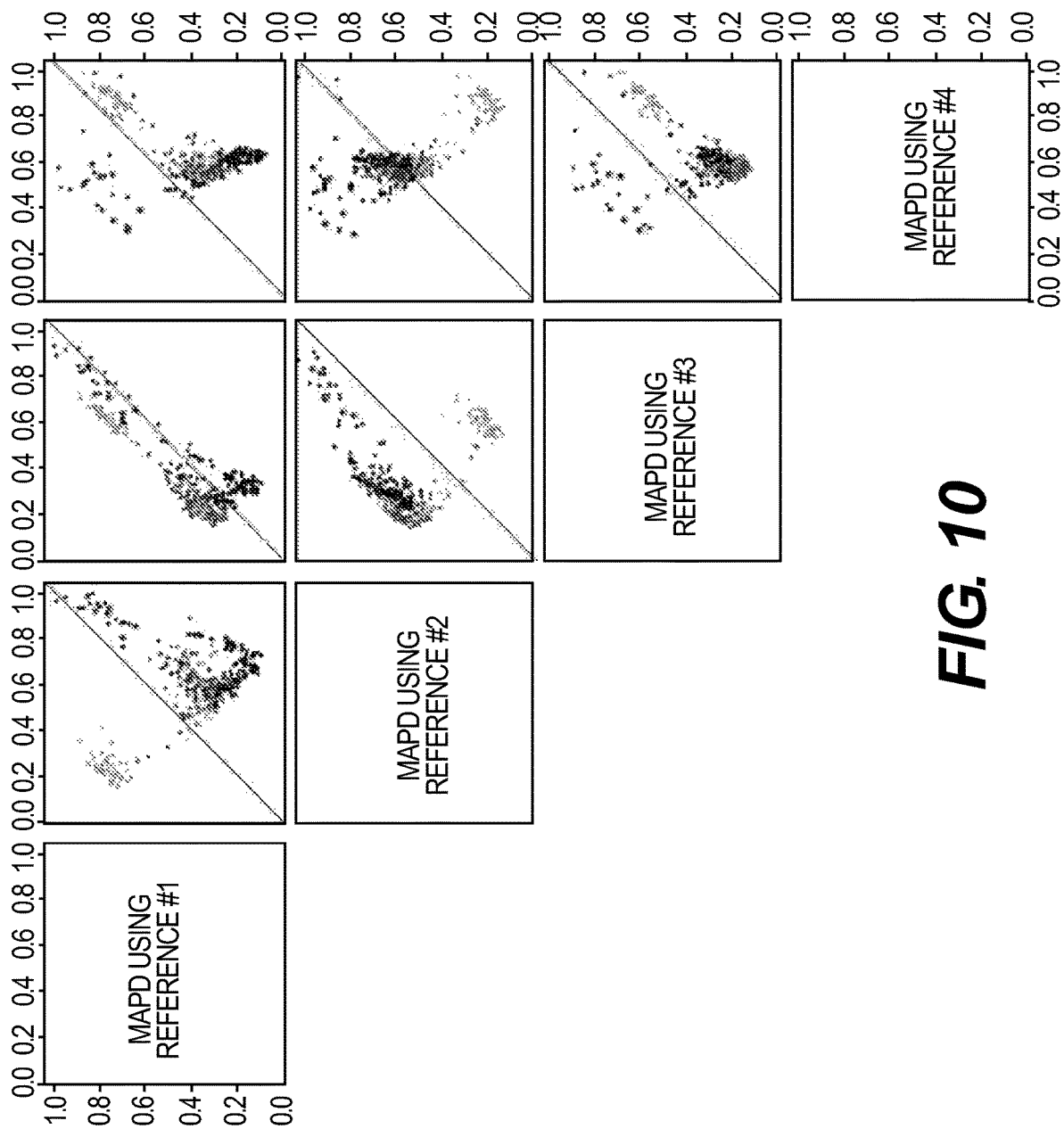
FIG. 10 depicts MAPD graphs illustrating application of the corrections for technical effects and batch effects to experiments, conducted in multiple batches, in accordance with various embodiments of the present disclosure.

FIGS. 9 and 10 depict MAPD graphs illustrating application of the corrections for technical effects and batch effects to experiments, conducted in multiple batches, according to embodiments of the present disclosure. As shown in FIGS. 9 and 10, MAPD after normalization improves through correction based on pool correction, amplicon GC correction, and insertion length correction. FIG. 10 also depicts MAPD graphs illustrating batch effects remaining after application of the correction for technical effects using different reference sets to normalize the tile, pool, and/or length effects, according to embodiments of the present disclosure.

As may be apparent from FIG. 10, batch effects may remain after correction, and the experiments show a multi-dimensional space of continuous batch effects. After application of pool correction, amplicon GC correction, and insertion length correction, some batch effects may not be characterized. Batch effects may remain because there may not be samples with normal copy numbers for constructing "local" references for every populated batch effect (space pocket). Thus, more pre-processing may be needed to account for additional batch effects.

Exemplary Principal Components Based Data Correction:

Each experiment may represent a vector of amplicon read counts (after some corrections may be applied). Thus, each experiment may reside in a particular location in a multi-dimensional space. The direction that has a maximal variance among all the experiments in the multi-dimensional space may capture the most prominent batch effect. A next direction of maximal variance, which may be orthogonal to the direction that has the maximal variance, may capture the next level of prominent batch effect. This process may be repeated to capture a number of prominent batch effects. Through principal components analysis, a projection of each experiment to the first direction may be eigenvectors, which correspond to batch effects. The eigenvectors may be calculated and adjusted to zero, and thus, may correct the most prominent batch effects.

Eigenvectors may not reflect the true copy number variation between samples used for different experiments. For example, if batch effects are prominent enough, the batch effects may dominate the first few principal components so that the data correction based on the top principal components may not affect a signal for a true copy number change. Further, it may be possible to reduce the true copy number change impact of the top principal components by carrying out principal component analysis ("PCA") with differences in read counts between adjacent amplicons instead of using amplicon read counts themselves.

Figure 11:
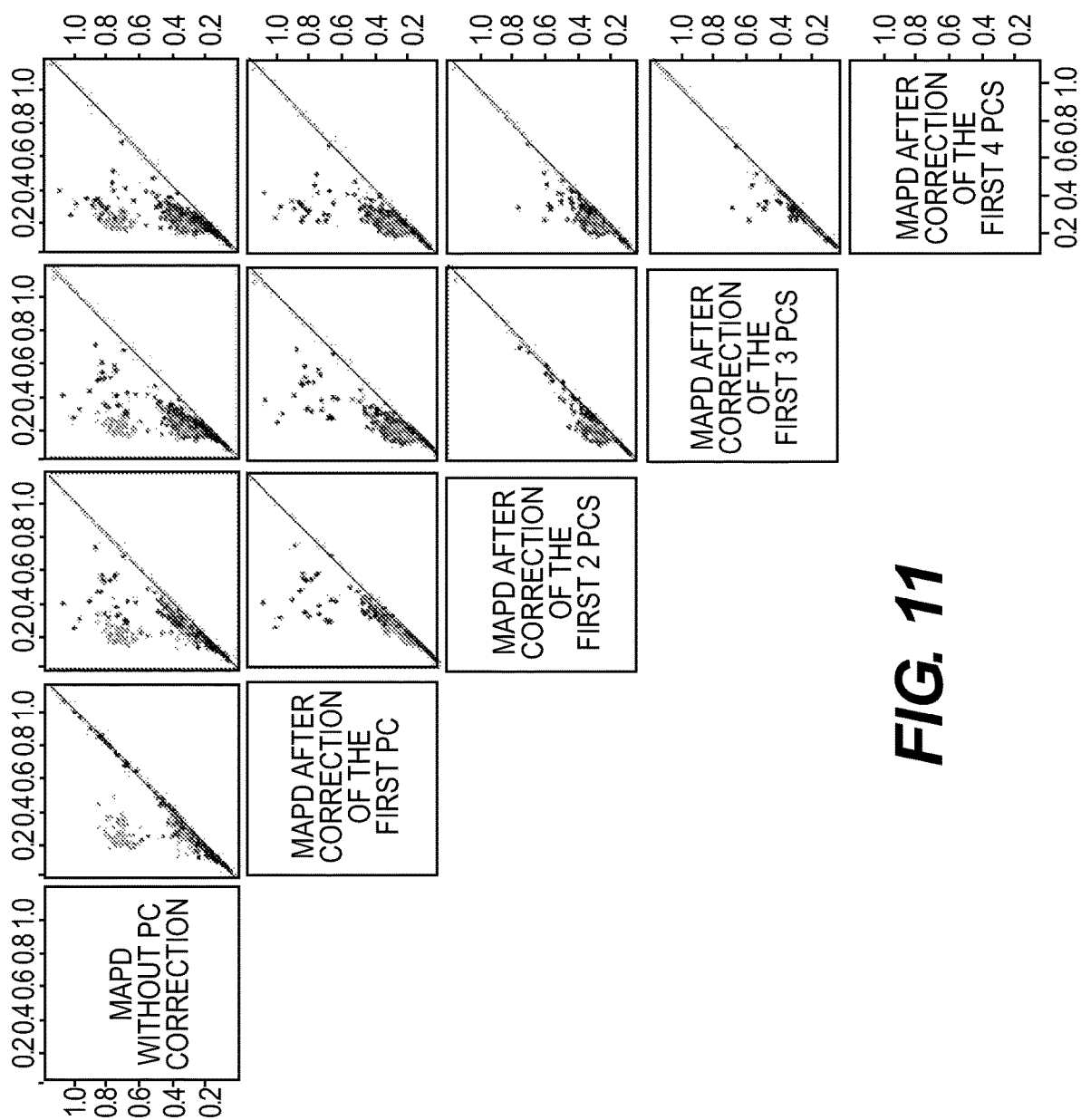
FIG. 11 depicts graphs illustrating improvement from applying corrections for technical effects and batch effects, in accordance with various embodiments of the present disclosure.
Figure 12:
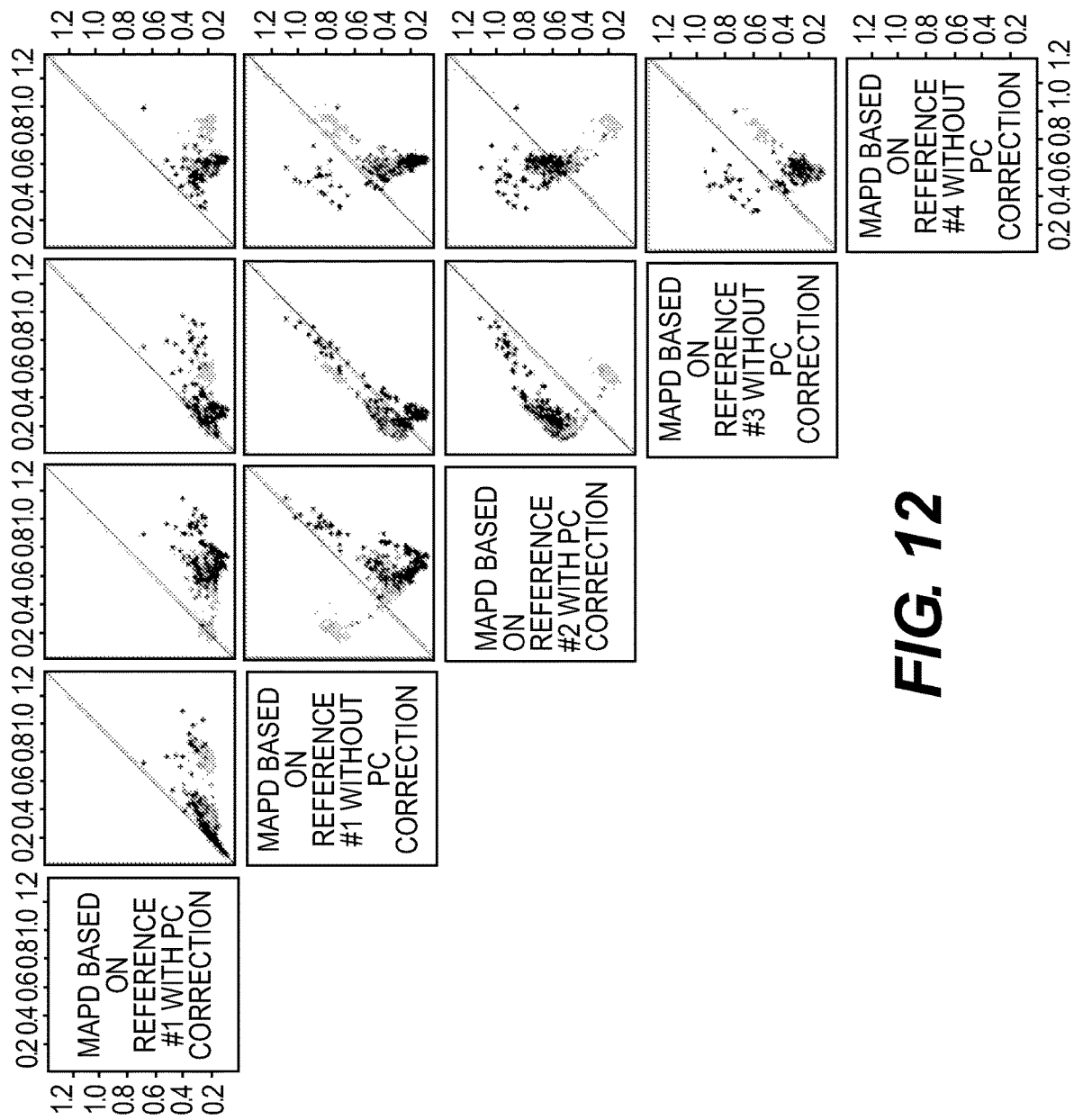
FIG. 12 depicts graphs illustrating improvement from applying corrections for technical effects and batch effects, in accordance with various embodiments of the present disclosure.

FIGS. 11 and 12 depict graphs illustrating improvement from applying corrections for technical effects and batch effects, in accordance with various embodiments of the present disclosure. FIGS. 11 and 12 depict principal component analysis results from various sets of genomic regions designated overexpressor of cationic peroxidase 2 ("OCP2").

As shown in FIG. 11, applying the batch effects correction improves the median absolute pairwise difference ("MAPD") as principal component based corrections are applied. FIG. 12 depicts a comparison of MAPD after principal component correction, using a standard reference, to MAPD without principal component correction, based on different sets of references.

Figure 13A:
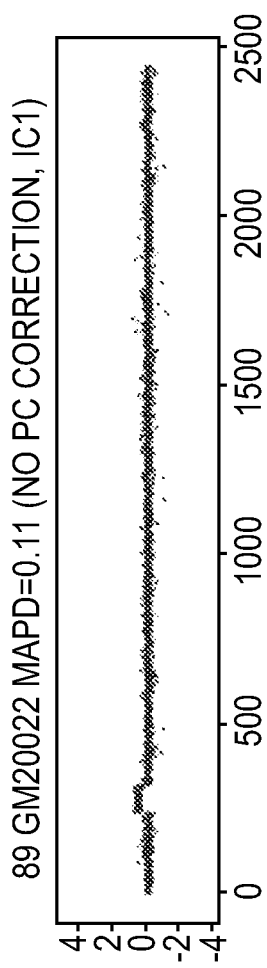
Figure 13B:
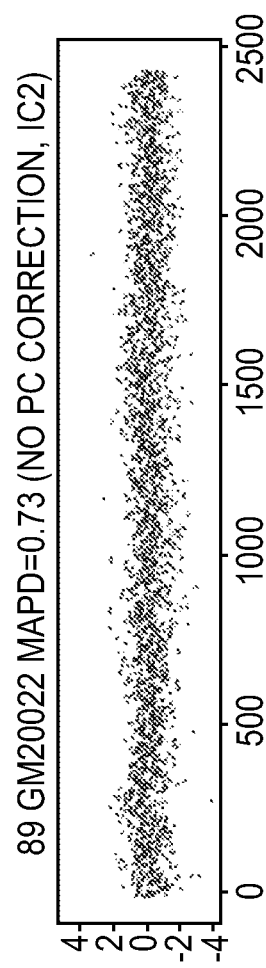
Figure 13E:
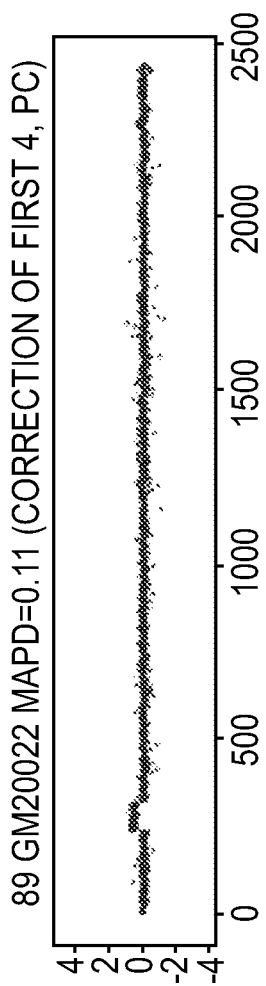

FIGS. 13A-13E provide comparisons of example samples with and without batch effects correction, according to embodiments of the present disclosure. FIGS. 13A-13E show samples prepared using multiplex amplification to generate a plurality of amplicons from a set of genomic regions designated 89 gm20022. As shown in FIGS. 13A-13D, without principal component correct, the median absolute pairwise differences ("MAPDs") are 0.11, 0.73, 0.32, and 0.63, respectively. Applying the batch effects correction improves the MAPD to 0.11, as shown in FIG. 13E.

Figure 14A:
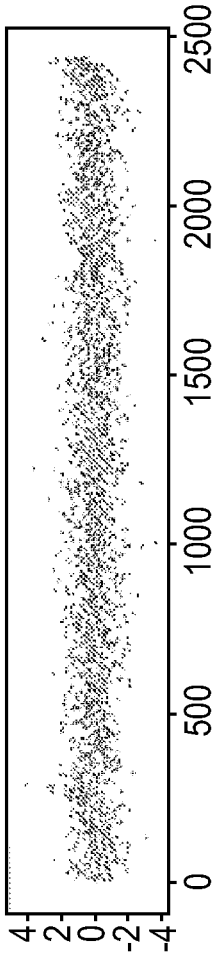
FIGS. 14A-14E depict graphs illustrating comparisons of example samples with and without batch effects correction, in accordance with various embodiments of the present disclosure.
Figure 14B:
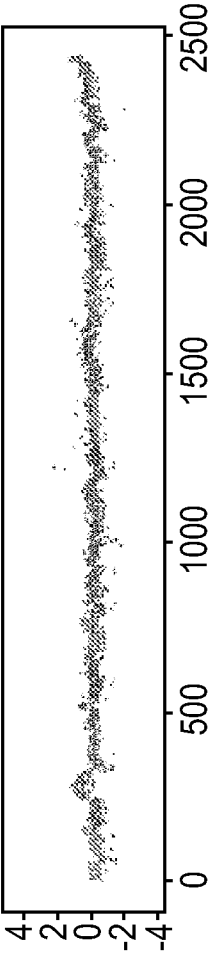
Figure 14C:
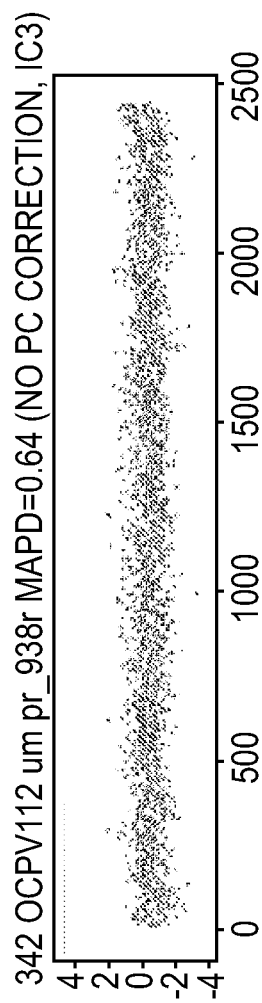
Figure 14D:
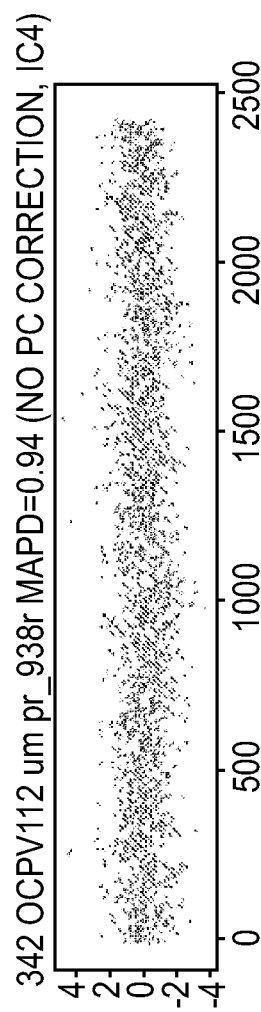
Figure 14E:
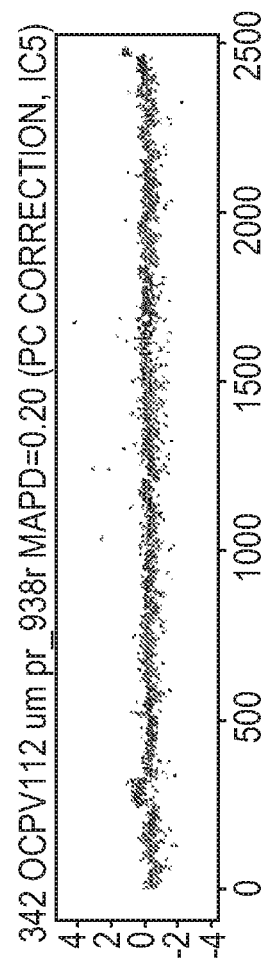

FIGS. 14A-14E provide comparisons of example samples with and without batch effects correction, according to embodiments of the present disclosure. FIGS. 14A-14E show samples prepared using multiplex amplification to generate a plurality of amplicons from a set of genomic regions designated 342 ocpv1i2 um pr_038r. As shown in FIGS. 14A-14D, without principal component correct, the MAPDs are 0.83, 0.23, 0.64, and 0.94, respectively. Applying the batch effects correction improves the MAPD to 0.20, as shown in FIG. 14E.

Figure 15C:
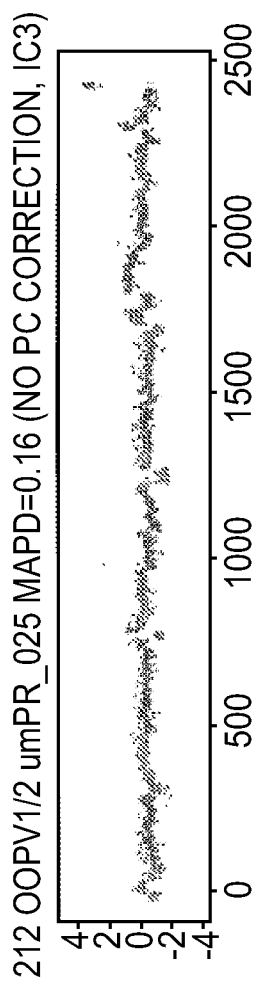
Figure 15D:
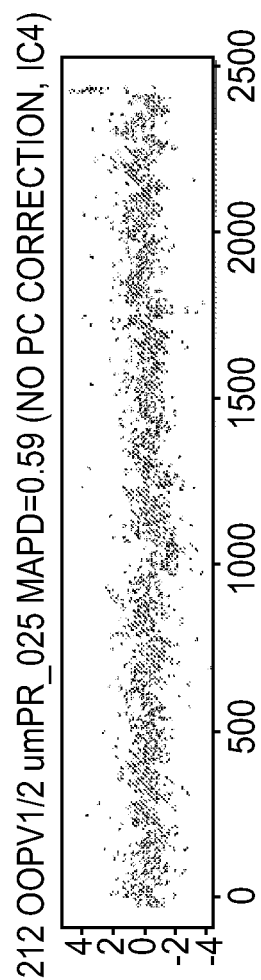
Figure 15E:
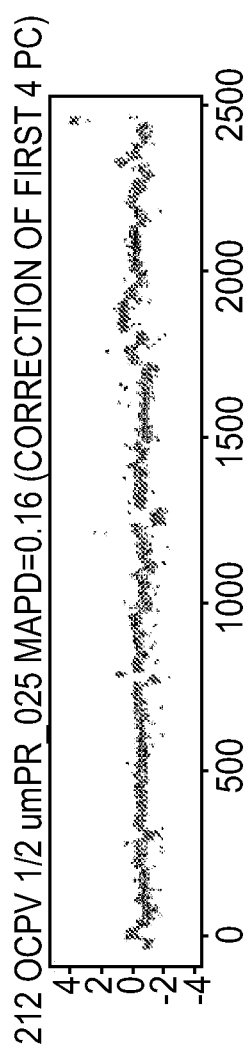

FIGS. 15A-15E provide comparisons of example samples with and without batch effects correction, according to embodiments of the present disclosure. FIGS. 15A-15E show samples prepared using multiplex amplification to generate a plurality of amplicons from a set of genomic regions designated 342 ocpv1i2 um pr_025. As shown in FIGS. 15A-15D, without principal component correct, the MAPDs are 0.24, 0.56, 0.16, and 0.59, respectively. Applying the batch effects correction improves the MAPD to 0.16, as shown in FIG. 15E.

Figure 16C:
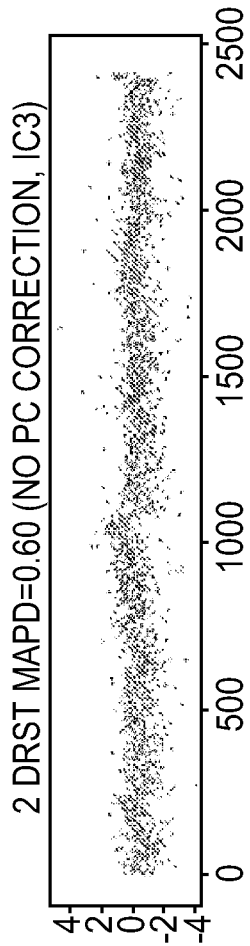
Figure 16D:
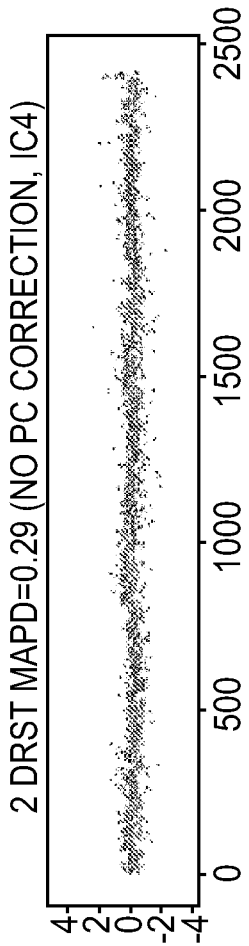
Figure 16E:
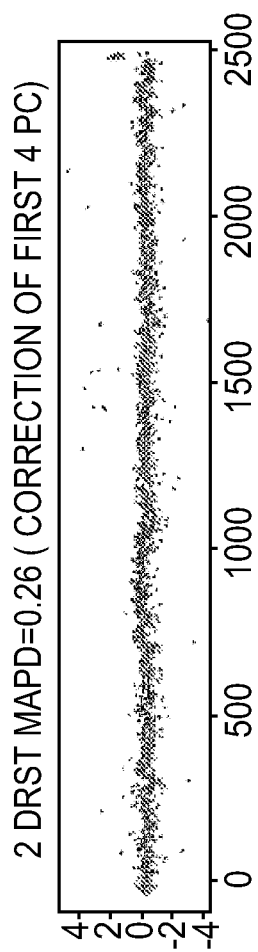

FIGS. 16A-16E provide comparisons of example samples with and without batch effects correction, according to embodiments of the present disclosure. FIGS. 16A-16E show samples prepared using multiplex amplification to generate a plurality of amplicons from a set of genomic regions designated 2 drst. As shown in FIGS. 16A-16D, without principal component correct, the MAPDs are 0.70, 0.89, 0.60, and 0.29, respectively. Applying the batch effects correction improves the MAPD to 0.26, as shown in FIG. 16E.

Figure 17:
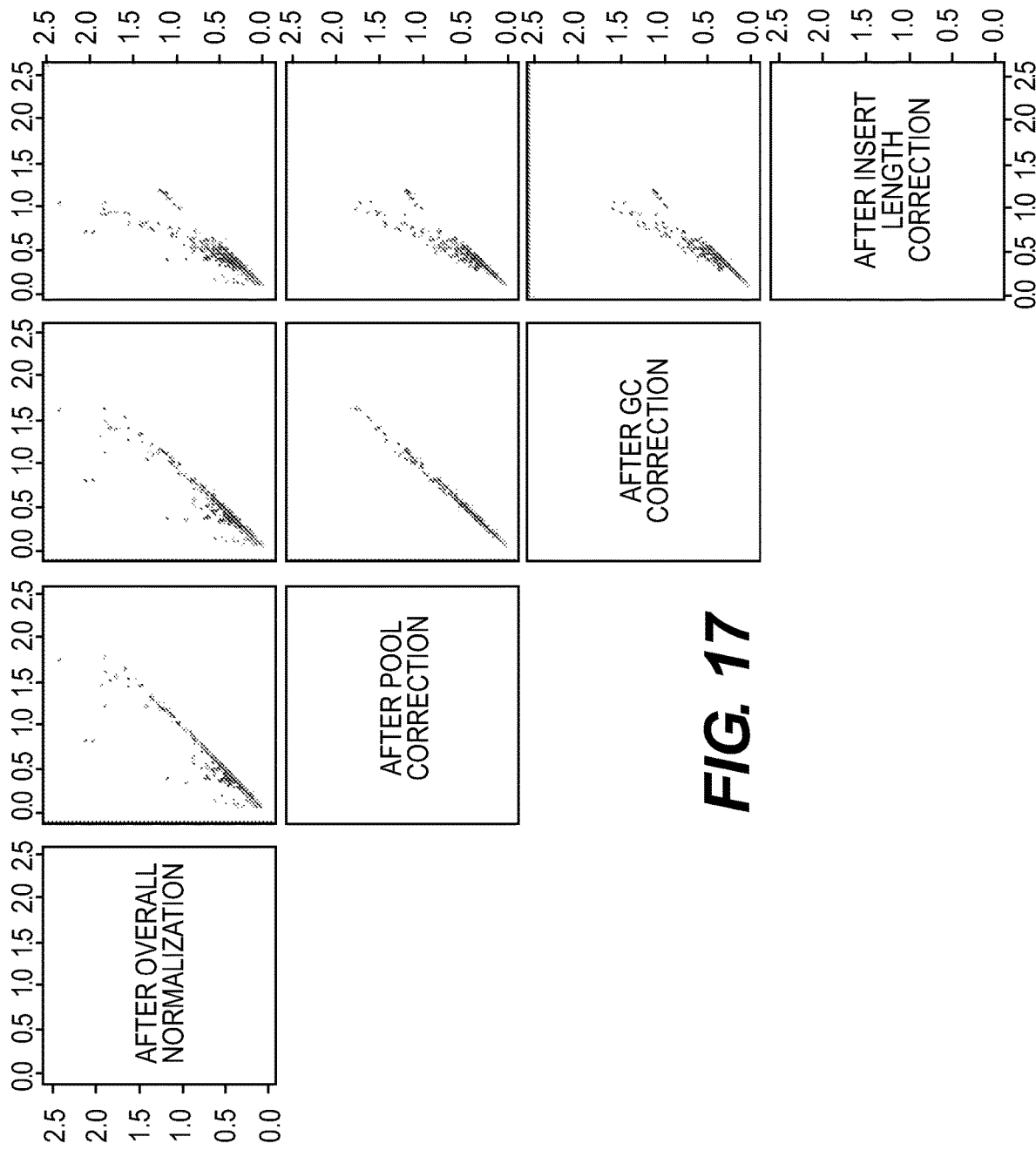
FIG. 17 depicts MAPD graphs illustrating application of the corrections for technical effects and batch effects to experiments, conducted in multiple batches from a set of genomic regions designated overexpressor of cationic peroxidase 3 ("OCP3"), in accordance with various embodiments of the present disclosure.

FIG. 17 depicts MAPD graphs illustrating application of the corrections for technical effects and batch effects to experiments, conducted in multiple batches, according to embodiments of the present disclosure. As shown in FIG. 17, MAPD after normalization improves through correction based on pool correction, amplicon GC correction, and insertion length correction.

Figure 18:
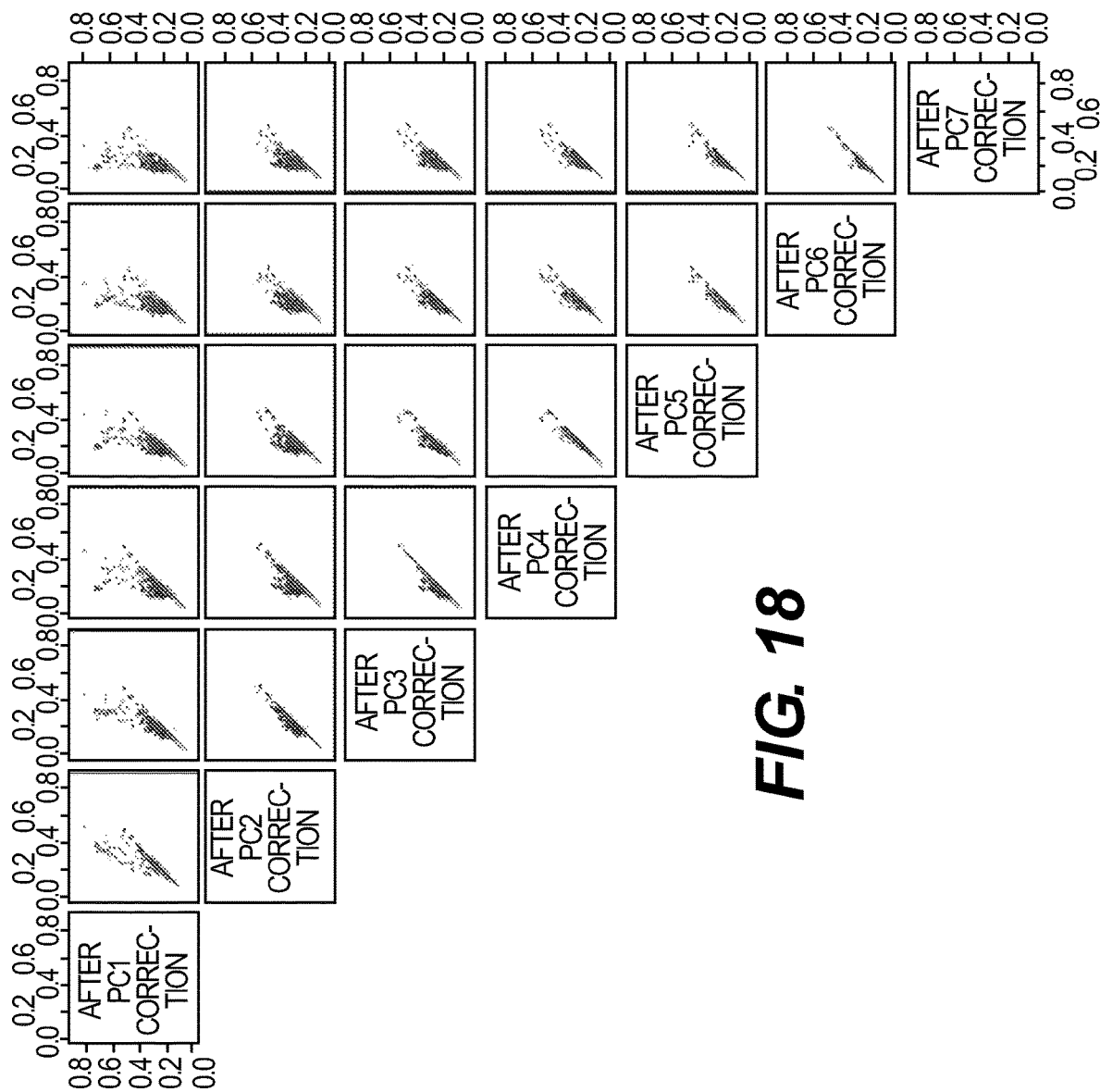
FIG. 18 depicts graphs illustrating improvement from applying corrections for technical effects and batch effects from a set of genomic regions designated OCP3, in accordance with various embodiments of the present disclosure.

FIG. 18 depicts graphs illustrating improvement from applying corrections for technical effects and batch effects from a set of genomic regions designated OCP3, in accordance with various embodiments of the present disclosure. FIG. 18 depicts principal component analysis results from various sets of genomic regions designated OCP3. As shown in FIG. 18, applying the batch effects correction improves the median absolute pairwise difference ("MAPD") as principal component based corrections are applied.

FIGS. 19A and 19B provide comparisons of example samples with and without pre-preprocessing, in accordance with various embodiments of the present disclosure. FIGS. 19A and 19B show a sample prepared using multiplex amplification to generate a plurality of amplicons from a set of genomic regions designated ocpv1i2_um_66. As shown in FIGS. 19A and 19B, applying pre-processing, after overall normalization, improves the MAPD from 0.835 to 0.393.

Figure 20A:
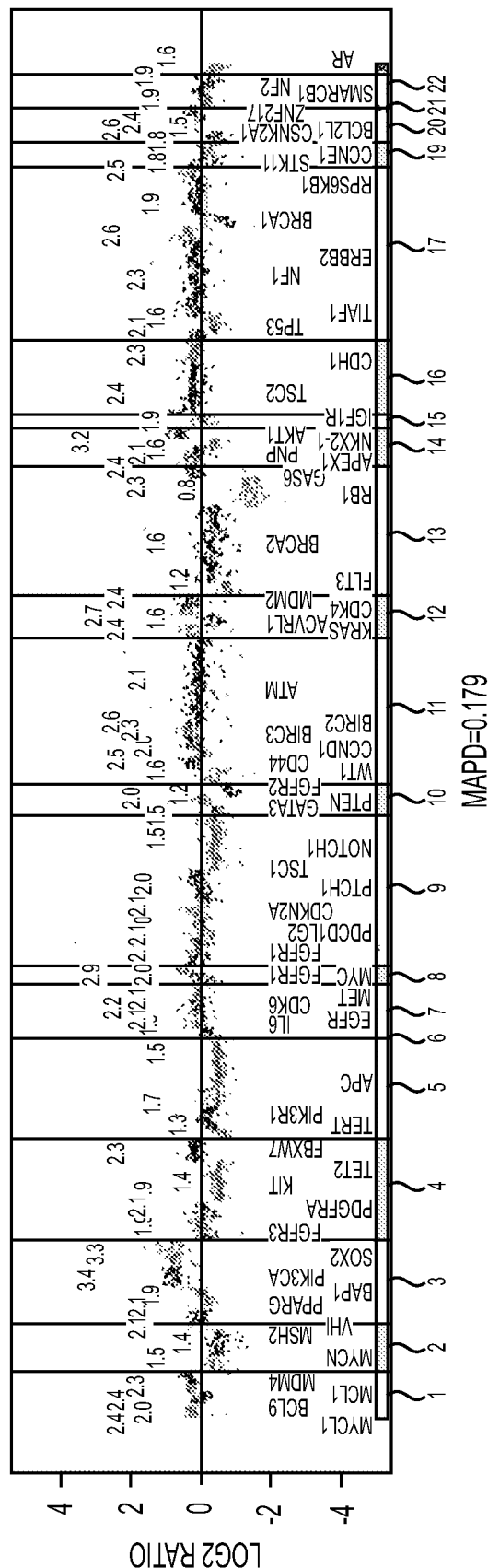
FIGS. 20A and 20B depict graphs illustrating comparisons of example samples with and without pre-preprocessing, in accordance with various embodiments of the present disclosure.
Figure 20B:
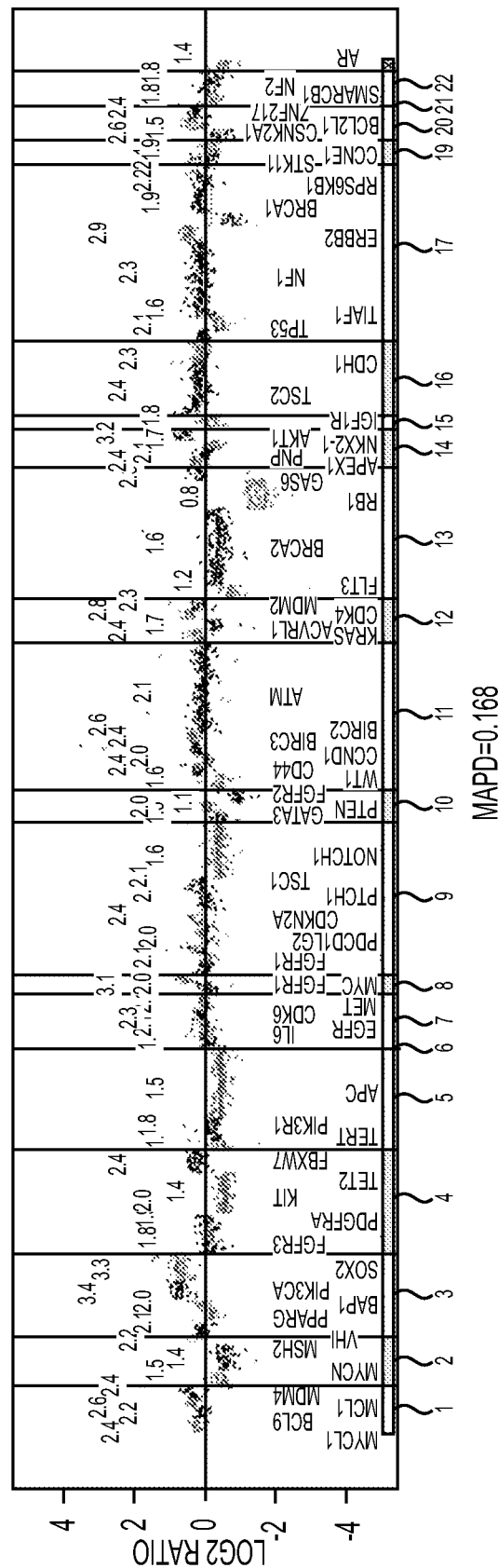

FIGS. 20A and 20B provide comparisons of example samples with and without pre-preprocessing, in accordance with various embodiments of the present disclosure. FIGS. 20A and 20B show another sample prepared using multiplex amplification to generate a plurality of amplicons from a set of genomic regions designated ocpv1i2_um_66. As shown in FIGS. 20A and 20B, applying pre-processing, after overall normalization, improves the MAPD from 0.179 to 0.168.

Figure 21B:
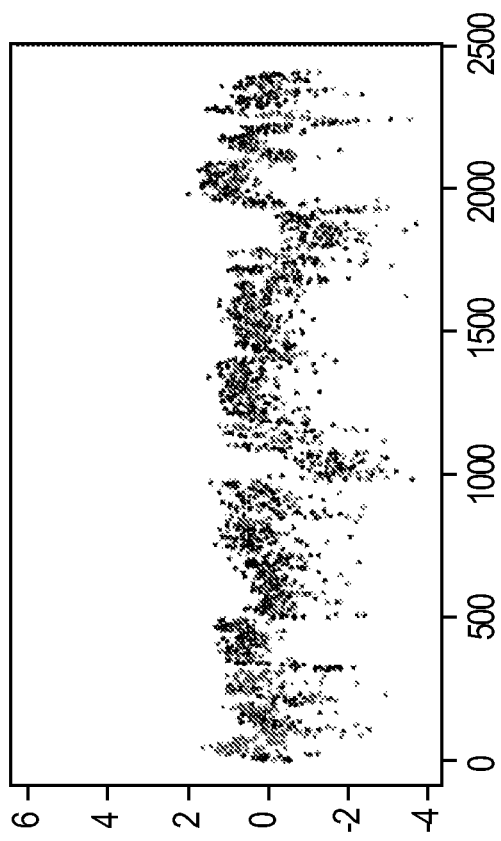
FIGS. 21A and 21B depict graphs illustrating comparisons of example samples with and without pre-preprocessing, in accordance with various embodiments of the present disclosure.
Figure 21A:
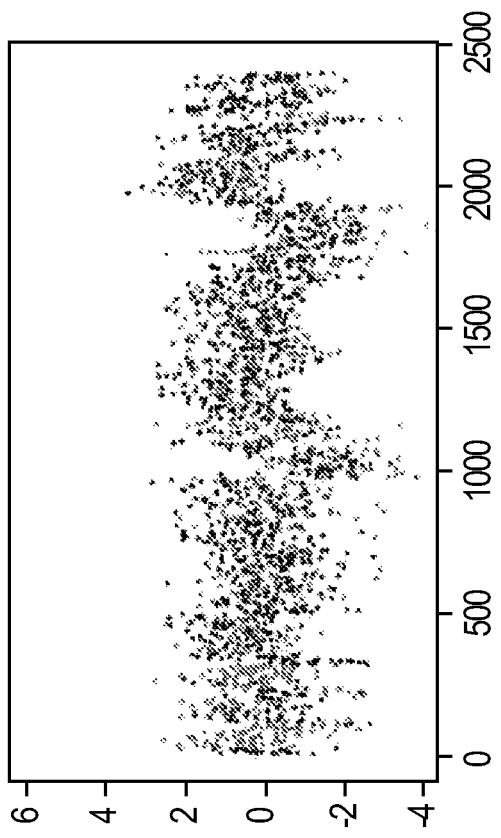

FIGS. 21A and 21B provide comparisons of example samples with and without pre-preprocessing, in accordance with various embodiments of the present disclosure. FIGS. 21A and 21B show a sample prepared using multiplex amplification to generate a plurality of amplicons from a set of genomic regions designated ocpv1i2_um_28. As shown in FIGS. 21A and 21B, applying pre-processing, after overall normalization, improves the MAPD from 0.781 to 0.377.

Figure 22A:
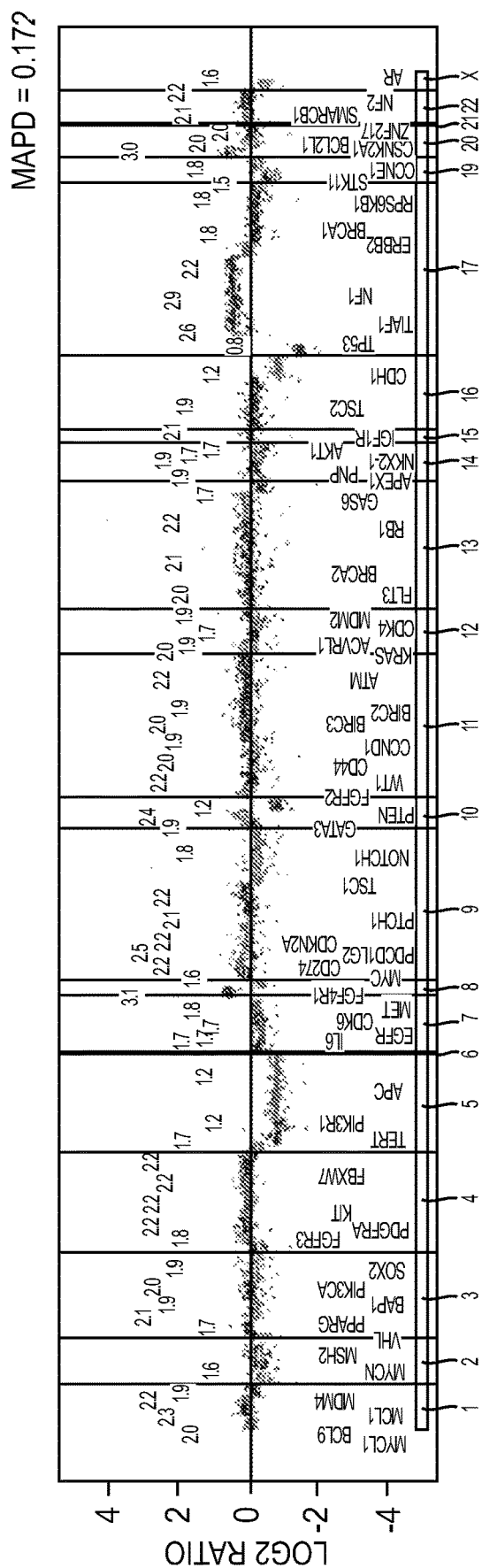
FIGS. 22A and 22B depict graphs illustrating comparisons of example samples with and without pre-preprocessing, in accordance with various embodiments of the present disclosure.
Figure 22B:
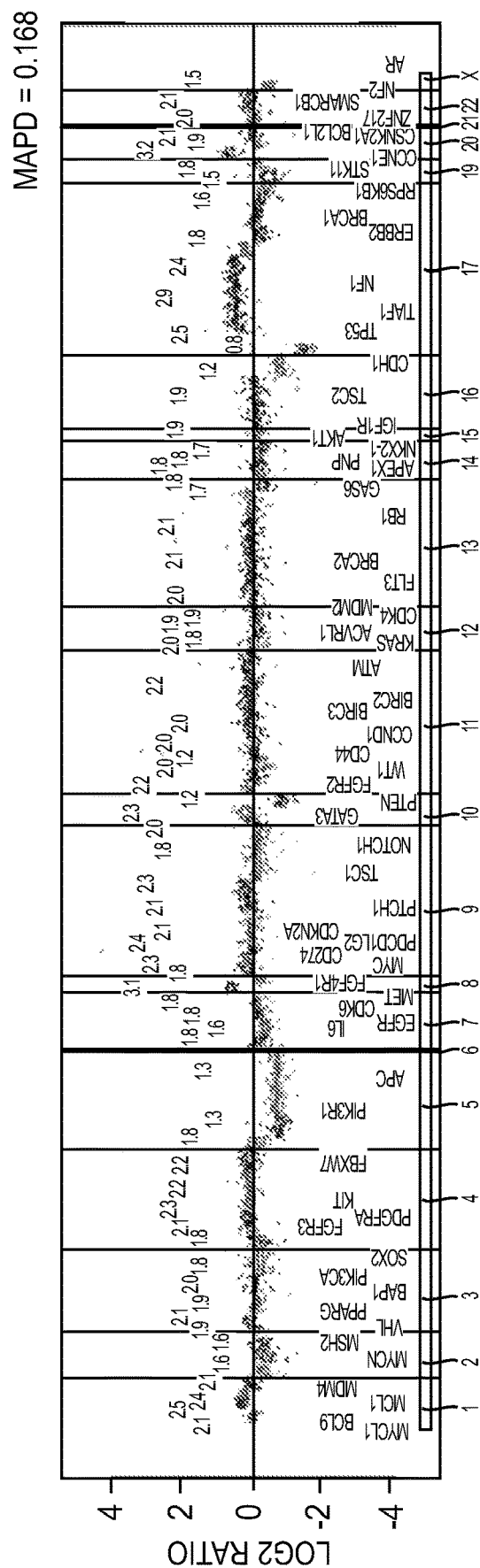

FIGS. 22A and 22B provide comparisons of example samples with and without pre-preprocessing, in accordance with various embodiments of the present disclosure. FIGS. 22A and 22B show another sample prepared using multiplex amplification to generate a plurality of amplicons from a set of genomic regions designated ocpv1i2_um_28. As shown in FIGS. 22A and 22B, applying pre-processing, after overall normalization, improves the MAPD from 0.172 to 0.168.

Figure 23A:
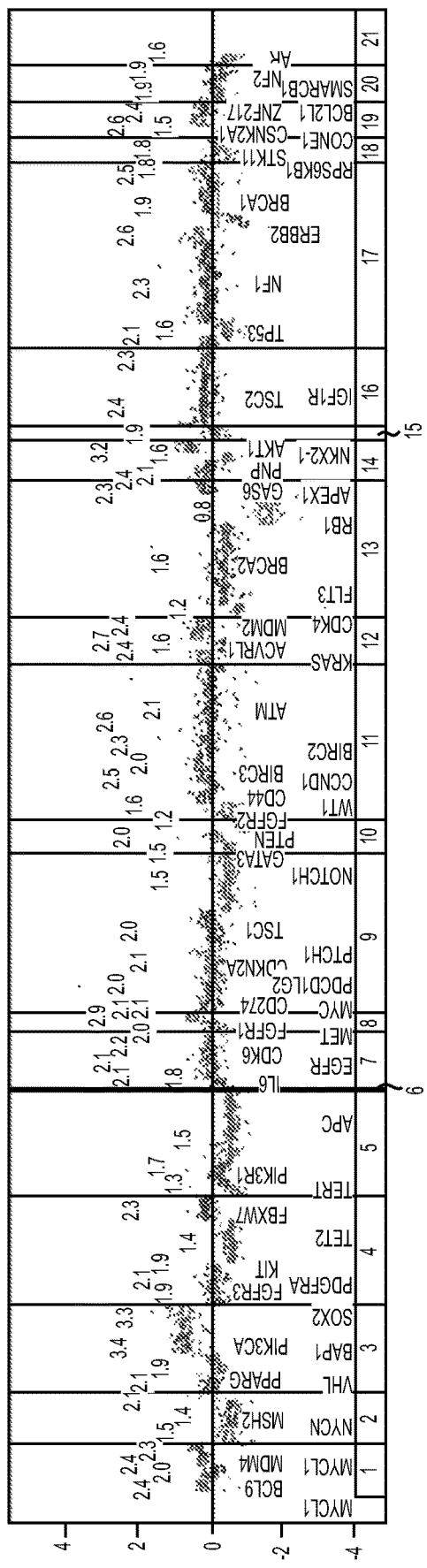
FIGS. 23A and 23B depict graphs illustrating comparisons of example samples with and without batch effects correction, in accordance with various embodiments of the present disclosure.
Figure 23B:
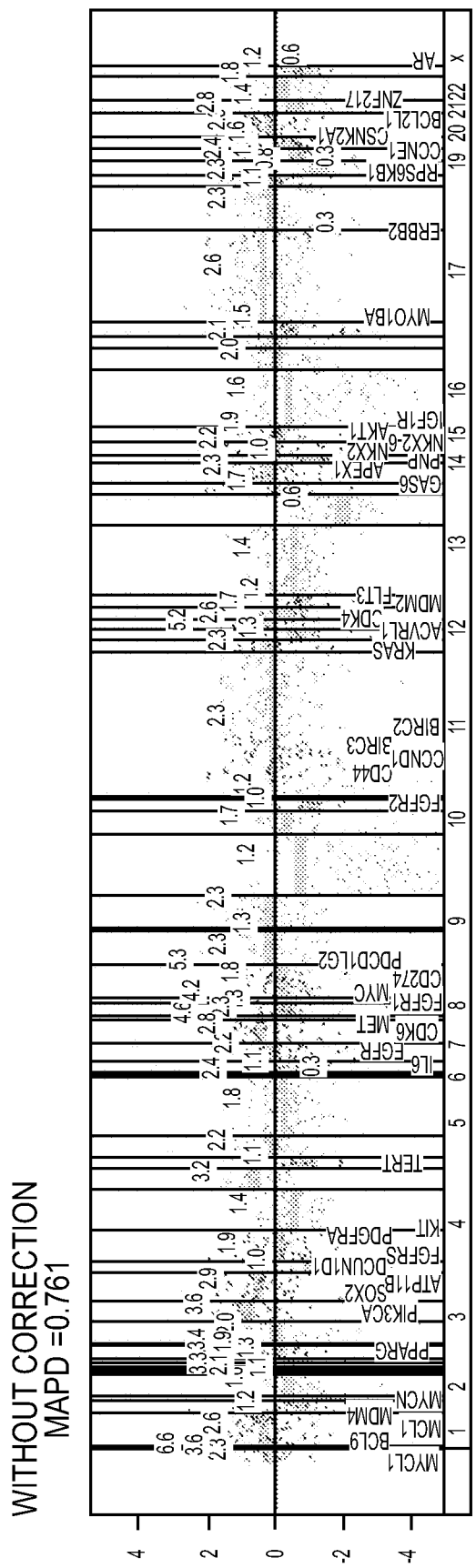

FIGS. 23A, 23B, 24A, and 24B provide comparisons of example samples with and without batch effects correction, in accordance with various embodiments of the present disclosure. FIGS. 23A and 23B show a sample prepared using multiplex amplification to generate a plurality of amplicons from a set of genomic regions designated OCP2.

Figure 24A:
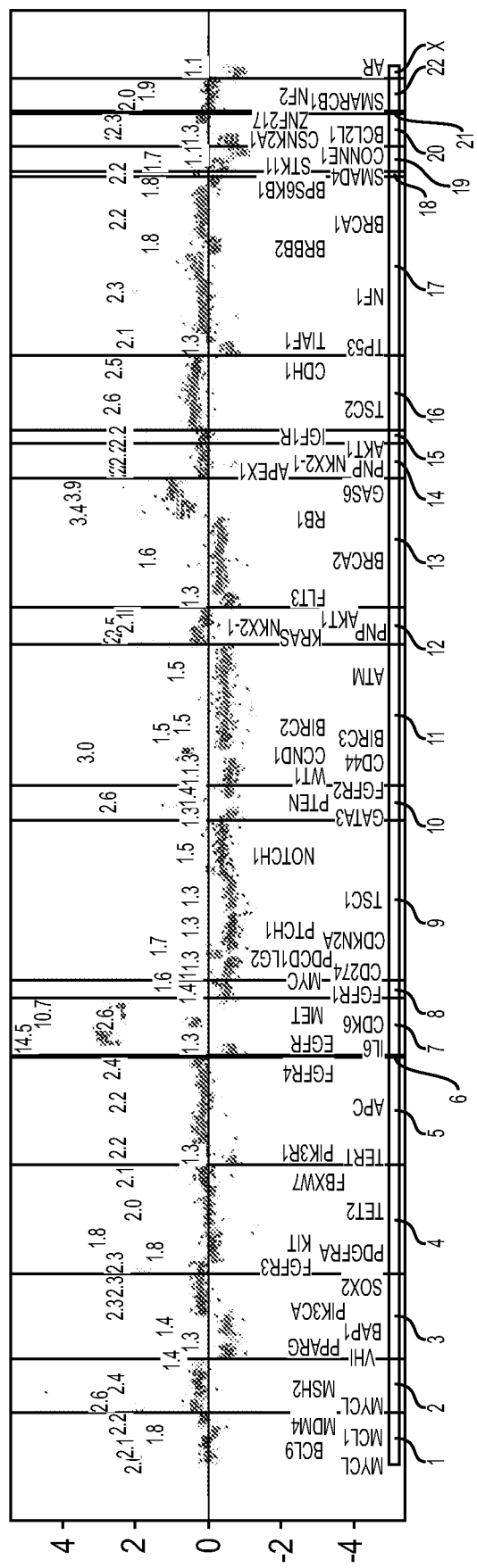
FIGS. 24A and 24B depict graphs illustrating comparisons of example samples with and without batch effects correction, in accordance with various embodiments of the present disclosure.
Figure 24B:
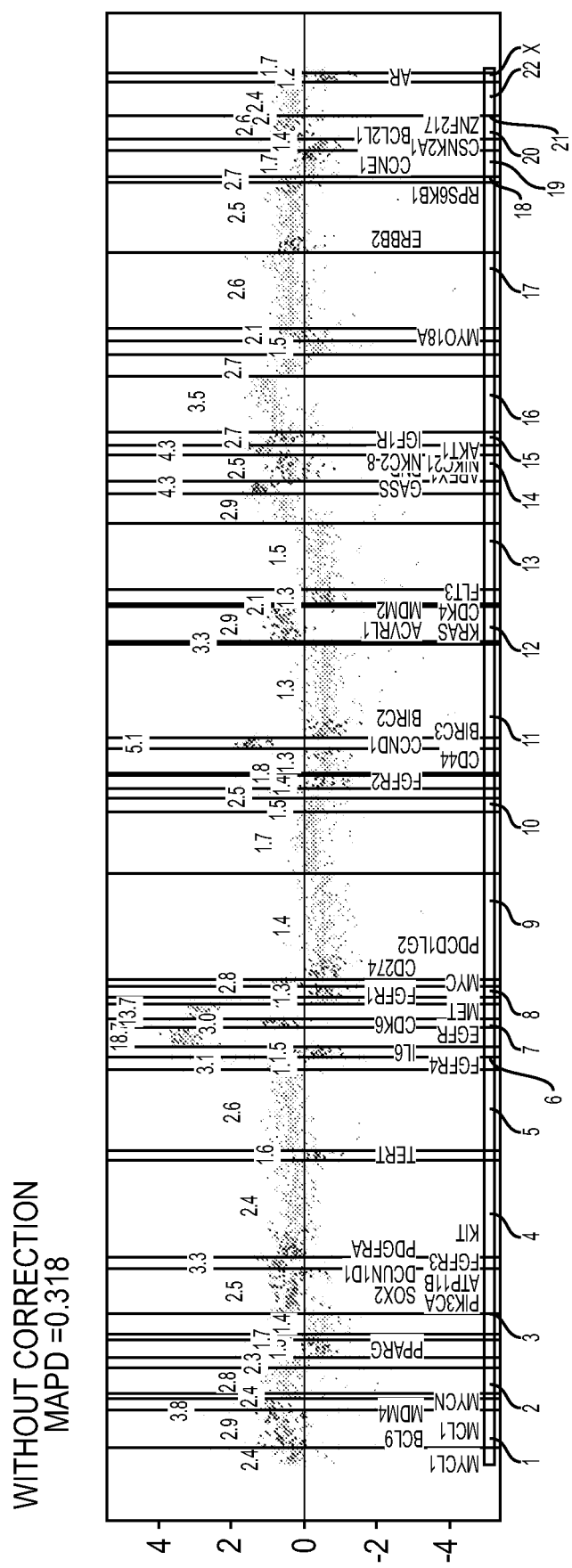

Applying the batch effects correction improves the median absolute pairwise difference (MAPD) from 0.761 to 0.179. FIGS. 24A and 24B show a sample prepared using multiplex amplification to generate a plurality of amplicons from another set of genomic regions designated OCP3. Applying the batch effects correction improves MAPD from 0.318 to 0.119.

In various embodiments, the methods of the present disclosure may be implemented in a software program and applications written in conventional programming languages such as C, C++, etc.

While the present disclosure is described in conjunction with various embodiments, it is not intended that the present teachings be limited to such embodiments. On the contrary, the present disclosure encompasses various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

The embodiments described herein, may be practiced with other computer system configurations including handheld devices, microprocessor systems, microprocessor-based or programmable consumer electronics, minicomputers, mainframe computers, and the like. The embodiments may also be practiced in distributing computing environments where tasks are performed by remote processing devices that are linked through a network.

It should also be understood that the embodiments described herein may employ various computer-implemented operations involving data stored in computer systems. These operations may be those requiring physical manipulation of physical quantities. Usually, though not necessarily, these quantities may take the form of electrical or magnetic signals capable of being stored, transferred, combined, compared, and otherwise manipulated. Further, the manipulations performed may often be referred to in terms, such as producing, identifying, determining, or comparing.

Any of the operations that form part of the embodiments described herein may be useful machine operations. The embodiments, described herein, also relate to a device or an apparatus for performing these operations. The systems and methods described herein may be specially constructed for the required purposes or it may be a general purpose computer selectively activated or configured by a computer program stored in the computer. In particular, various general purpose machines may be used with computer programs written in accordance with the teachings herein, or it may be more convenient to construct a more specialized apparatus to perform the required operations.

Certain embodiments may also be embodied as computer-readable code on a computer readable medium. The computer-readable medium may be any data storage device that can store data, which can thereafter be read by a computer system. Examples of the computer-readable medium may include hard disk drives, solid state drives, network attached storage (NAS), read-only memory, random-access memory, CD-ROMs, CD-Rs, CD-RWs, magnetic tapes, and other optical and non-optical data storage devices. The computer-readable medium may also be distributed over a network coupled computer systems so that the computer-readable code is stored and executed in a distributed fashion.

Unless otherwise specifically designated herein, terms, techniques, and symbols of biochemistry, cell biology, genetics, molecular biology, nucleic acid chemistry, nucleic acid sequencing, and organic chemistry used herein may follow those of standard treatises and texts in the relevant field.

Although the present description described in detail certain embodiments, other embodiments are also possible and within the scope of the present disclosure. For example, those skilled in the art may appreciate from the present description that the present teachings may be implemented in a variety of forms, and that the various embodiments may be implemented alone or in combination. Variations and modifications will be apparent to those skilled in the art from consideration of the specification and figures and practice of the teachings described in the specification and figures, and the claims.

The invention claimed is:

1. A computer-implemented method for identifying a copy number variation, the method comprising:
obtaining, for each training sample of a plurality of training samples in an NGS assay targeting a plurality of amplicons, a plurality of training reads, wherein the plurality of training samples include normal samples having known ploidy, wherein some of the plurality of training samples are prepared in different batches of a plurality of batches than are others of the plurality of training samples;
mapping, for each training sample of the plurality of training samples, the plurality of training reads to a nucleic acid reference sequence corresponding to amplicons of the training sample;
calculating, for each training sample of the plurality of training samples, amplicon coverages and total reads for the training sample, wherein an amplicon coverage is a number of reads mapped to an amplicon and the total reads is a number of mapped reads;
representing amplicon coverages for each training sample of the plurality of training samples as a vector to obtain a plurality of vectors representing amplicon coverages of the plurality of training samples in the plurality of batches;
determining values of a batch effect by applying a principal components analysis to the plurality of vectors, wherein each principal component is used to obtain a vector of batch effect values;
obtaining, from each test sample of a plurality of test samples in the NGS assay targeting the plurality of amplicons, a plurality of reads of a plurality of amplicons based on amplified target regions of the test sample;
mapping, for each test sample of the plurality of test samples, the plurality of reads to a reference sequence, the reference sequence including one or more nucleic acid sequences corresponding to the amplified target regions;
calculating, for each test sample of the plurality of test samples, amplicon coverages and total reads for the test sample;

representing amplicon coverages for each test sample of the plurality of test samples as a test vector to obtain a plurality of test vectors representing amplicon coverages of the plurality of test samples;

projecting each of the plurality of test vectors onto the principal components identified by the principal components analysis of the training samples to determine a plurality of scaling factors;

calculating corrected amplicon coverages by applying a batch effect correction for each test sample based on the calculated amplicon coverages for the test sample, the calculated total reads for the test sample, the scaling factor determined for the test sample and the batch effect values corresponding to the principal components determined for the training sample; and identifying the copy number variation of the test sample based on a likelihood of a ploidy state for the corrected amplicon coverages.

2. The method of claim 1, further comprising:

amplifying the target regions of nucleic acids isolated from the test sample suspected of having one or more genetic abnormalities;

producing the plurality of amplicons based on the amplified target regions; and sequencing the plurality of amplicons to obtain the plurality of reads.

3. The method of claim 2, wherein amplifying the target regions of nucleic acids isolated from the test sample suspected of having one or more genetic abnormalities includes multiplex amplification.

4. The method of claim 1, further comprising:

determining a maximum score path for the plurality of amplicons based on the likelihoods calculated for a range of ploidy states; and identifying the copy number variations based on the maximum score path.

5. The method of claim 4, further comprising:

normalizing, prior to calculating the likelihoods for the maximum score path, the corrected amplicon coverages based on the total reads.

6. The method of claim 1, wherein the step of calculating corrected amplicon coverages further includes determining a logarithm of the corrected copy number for an i-th amplicon based on a product of the scaling factor and a logarithm of the batch effect value determined for the i-th amplicon.

* * * * *